United States Patent
Nakamura et al.

(10) Patent No.: US 10,690,596 B2
(45) Date of Patent: Jun. 23, 2020

(54) SURFACE PLASMON-ENHANCED FLUORESCENCE MEASUREMENT DEVICE AND SURFACE PLASMON-ENHANCED FLUORESCENCE MEASUREMENT METHOD

(71) Applicant: Konica Minolta, Inc., Tokyo (JP)

(72) Inventors: Yukito Nakamura, Saitama (JP); Kosuke Nagae, Tokyo (JP); Takatoshi Kaya, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 425 days.

(21) Appl. No.: 15/536,109

(22) PCT Filed: Dec. 1, 2015

(86) PCT No.: PCT/JP2015/083763
§ 371 (c)(1),
(2) Date: Jun. 14, 2017

(87) PCT Pub. No.: WO2016/098581
PCT Pub. Date: Jun. 23, 2016

(65) Prior Publication Data
US 2018/0017493 A1    Jan. 18, 2018

(30) Foreign Application Priority Data
Dec. 15, 2014 (JP) .................. 2014-253193

(51) Int. Cl.
*G01N 33/553* (2006.01)
*G01N 21/64* (2006.01)
(Continued)

(52) U.S. Cl.
CPC .......... *G01N 21/648* (2013.01); *G01J 3/0202* (2013.01); *G01J 3/0224* (2013.01);
(Continued)

(58) Field of Classification Search
CPC ............ G01N 21/648; G01N 21/6486; G01N 21/6428; G01N 21/6445; G01N 2021/6439; G01N 2021/6463
(Continued)

(56) References Cited

U.S. PATENT DOCUMENTS

| 6,274,872 B1 | 8/2001 | Katerkamp |
| 7,989,220 B2 | 8/2011 | Lakowicz et al. |

(Continued)

FOREIGN PATENT DOCUMENTS

| JP | 2000-515966 A | 11/2000 |
| JP | 2008-286778 A | 11/2008 |

(Continued)

OTHER PUBLICATIONS

International Patent Application No. PCT/JP2015/083763; Int'l Preliminary Report on Patentability; dated Jun. 29, 2017; 5 pages.
(Continued)

*Primary Examiner* — Christopher L Chin
(74) *Attorney, Agent, or Firm* — BakerHostetler

(57) ABSTRACT

The surface plasmon-enhanced fluorescence measurement device has: a light source that irradiates the diffraction grating with a linearly polarized excitation light; a rotating part that changes the direction of the optical axis of the excitation light with respect to the diffraction grating when seen in plan view, or changes the polarization direction of the excitation light with respect to the diffraction grating; a polarizer that extracts linearly polarized light from the fluorescence emitted from the fluorescent substance; and a light detection unit that detects the linearly polarized light extracted by the polarizer.

9 Claims, 13 Drawing Sheets

(51) Int. Cl.
*G01J 3/02* (2006.01)
*G01J 3/18* (2006.01)
*G01N 33/543* (2006.01)

(52) U.S. Cl.
CPC ............... *G01J 3/0237* (2013.01); *G01J 3/18* (2013.01); *G01N 21/6428* (2013.01); *G01N 21/6445* (2013.01); *G01N 33/54373* (2013.01); *G01N 33/553* (2013.01); *G01N 2021/6439* (2013.01); *G01N 2021/6463* (2013.01); *G01N 2201/0683* (2013.01)

(58) Field of Classification Search
USPC ......... 422/82.08, 82.11; 435/288.7; 436/172, 436/525, 805
See application file for complete search history.

(56) References Cited

U.S. PATENT DOCUMENTS

2005/0186565 A1   8/2005   Malak
2009/0045351 A1   2/2009   Smolyaninov et al.

FOREIGN PATENT DOCUMENTS

JP   2010-038624 A   2/2010
JP   2011-158369     8/2011

OTHER PUBLICATIONS

Keiko, Tawa et al.; "Optical microscopic observation of fluorescence enhanced by grating-coupled surface plasmon resonance"; Optics Express; vol. 16 No. 13; Jun. 2008; p. 9781-9790.
Bauch et al.; "Plasmon-Enhanced Fluorescence Biosensors: a Review"; Plasmonics; vol. 9 No. 4; Dec. 2013; p. 781-799.
European Patent Application No. 15869789.6; Extended Search Report; dated Nov. 7, 2017; 8 pages.
Japan Patent Application No. 2016-564769; Notice of Reasons for Refusal; dated May 28, 2019; 6 pages.
Tawa et al., "Optical microscopic observation of fluorescence enhanced by grating-coupled surface plasmon resonance", Optics Express, vol. 16, No. 13, pp. 9781-9790, Jun. 23, 2008.

SURFACE PLASMON-ENHANCED FLUORESCENCE MEASUREMENT DEVICE AND SURFACE PLASMON-ENHANCED FLUORESCENCE MEASUREMENT METHOD

TECHNICAL FIELD

The present invention relates to a surface plasmon-field enhanced fluorescence measurement apparatus and a surface plasmon-field enhanced fluorescence measurement method for detecting, utilizing surface plasmon resonance, the presence or an amount of an analyte contained in a sample.

BACKGROUND ART

In a clinical test or the like, highly sensitive and quantitative detection of a trace amount of analyte, such as a protein or DNA, would allow a quick understanding of a patient's condition and the subsequent his/her treatment. For this reason, there is a need for a method of detecting a trace amount of analyte highly sensitively and quantitatively.

As a highly sensitive method of detecting an analyte, surface plasmon-field enhanced fluorescence spectroscopy (hereinafter abbreviated as "SPFS") is known. SPFS utilizes surface plasmon resonance (hereinafter abbreviated as "SPR") generated upon irradiation of a metal film with light under predetermined conditions. A ligand (e.g., primary antibody) that can specifically bind to an analyte is immobilized above a metal film, thereby forming a reaction site for specifically capturing an analyte. When a sample containing an analyte is provided to the reaction site, the analyte binds to the reaction site. Then, when another ligand (e.g., secondary antibody) labeled with a fluorescent substance is provided to the reaction site, the analyte bound to the reaction site is labeled with the fluorescent substance. When the metal film is irradiated with excitation light under such conditions, the fluorescent substance that labels the analyte is excited by enhanced electric fields due to SPR to emit fluorescence. Thus, the presence or an amount of the analyte can be detected by detecting fluorescence. SPFS can detect an analyte highly sensitively since a fluorescent substance is excited by enhanced electric fields due to SPR.

SPFS is broadly categorized into prism coupling (PC)-SPFS and grating coupling (GC)-SPFS in accordance with a means for coupling excitation light and surface plasmon. PC-SPFS utilizes a prism formed on one surface of a metal film. In this method, excitation light and surface plasmon are coupled by total reflection of excitation light at an interface between the prism and the metal film. PC-SPFS, which is a mainstream method today, has a challenge of downsizing a measurement apparatus since a prism is used and an incident angle of excitation light on a metal film is large.

Meanwhile, GC-SPFS couples excitation light and surface plasmon utilizing a diffraction grating (see Patent Literature (hereinafter abbreviated as PTL) 1 and Non-Patent Literature (hereinafter abbreviated as NPL) 1). GC-SPFS can downsize a measurement apparatus compared with PC-SPFS, since a prism is not used and an incident angle of excitation light on a diffraction grating is small.

CITATION LIST

Patent Literature

PTL 1
Japanese Patent Application Laid-Open No. 2011-158369

Non-Patent Literature

NPL 1
Keiko Tawa, Hironobu Hori, Kenji Kintaka, Kazuyuki Kiyosue, Yoshiro Tatsu, and Junji Nishii, "Optical microscopic observation of fluorescence enhanced by grating-coupled surface plasmon resonance," Optics Express, Vol. 16, pp. 9781-9790

SUMMARY OF INVENTION

Technical Problem

As described above, although GC-SPFS has the advantage that a measurement apparatus can be downsized compared with PC-SPFS, GC-SPFS has not yet been vigorously studied compared with PC-SPFS. Accordingly, a measurement apparatus and a measurement method utilizing GC-SPFS have room for improvement in detection sensitivity.

An object of the present invention is to provide a measurement apparatus and a measurement method utilizing GC-SPFS that can detect an analyte with higher sensitively.

Solution to Problem

To achieve at least one of the aforementioned objects, a surface plasmon-field enhanced fluorescence measurement apparatus according to an embodiment of the present invention, configured to be equipped with a chip which includes a metal film where a diffraction grating is formed and which includes a ligand, for capturing an analyte to be labeled with a fluorescent substance, immobilized above the diffraction grating, and configured to detect the presence or an amount of the analyte by irradiating the diffraction grating with excitation light, the measurement apparatus includes: a light source configured to irradiate the diffraction grating with linearly polarized excitation light so that the fluorescent substance is excited by an enhanced electric field to emit fluorescence; a rotation section configured to change a direction of an optical axis of the excitation light relative to the diffraction grating in a plan view, or change a polarization direction of the excitation light relative to the diffraction grating; a polarizer for isolating linearly polarized light from fluorescence emitted from the fluorescent substance; and a light detection section configured to detect the linearly polarized light isolated by the polarizer.

Further, to achieve at least one of the aforementioned objects, a surface plasmon-field enhanced fluorescence measurement method according to an embodiment of the present invention, for detecting fluorescence emitted from a fluorescent substance, which labels an analyte and is excited by an electric field based on surface plasmon resonance, to detect the presence or an amount of an analyte, the measurement method includes: a first step of preparing a chip which has a metal film where a diffraction grating is formed and which has a ligand, for capturing an analyte to be labeled with a fluorescent substance, immobilized above the diffraction grating; a second step of irradiating the diffraction grating with linearly polarized excitation light, when a liquid containing the fluorescent substance is present on the metal film, so as to generate surface plasmon resonance in the diffraction grating; detecting linearly polarized first light with an angle of an oscillation direction of an electric field in the range of 0±30° relative to a plane and linearly polarized second light with an angle of an oscillation direction of an electric field in the range of 90±30° relative to the plane, in which the plane contains a normal line to a surface of the metal film and an optical axis of the excitation light, and the linearly polarized first light and the linearly polarized second light are contained in fluorescence emitted from the fluorescent substance; and changing the direction of the optical axis of the excitation light relative to the diffraction grating in a plan view or changing a polarization direction of the excitation light relative to the diffraction grating so that a difference value between a detected value of the first light and a detected value of the second light becomes zero; a third step of bringing the analyte labeled with the fluorescent substance into contact with the ligand immobilized above the metal film or labeling the analyte captured by the ligand immobilized above the metal film with the fluorescent substance; a fourth step of irradiating, after the second step and the third step, the diffraction grating with linearly polarized excitation light so as to generate surface plasmon resonance in the diffraction grating, and detecting linearly polarized third light with an angle of an oscillation direction of an electric field in the range of 0±30° relative to the plane and linearly polarized fourth light with an angle of an oscillation direction of an electric field in the range of 90±30° relative to the plane, in which the linearly polarized third light and the linearly polarized fourth light are contained in fluorescence emitted from the fluorescent substance; and a fifth step of calculating a difference value between a detected value of the third light and a detected value of the fourth light.

Advantageous Effects of Invention

According to the present invention, a measurement apparatus and a measurement method utilizing GC-SPFS can detect an analyte with higher sensitively.

DESCRIPTION OF EMBODIMENTS

Embodiments of the present invention will be described in detail hereinafter with reference to the accompanying drawings.

Embodiment 1

Figure 1:
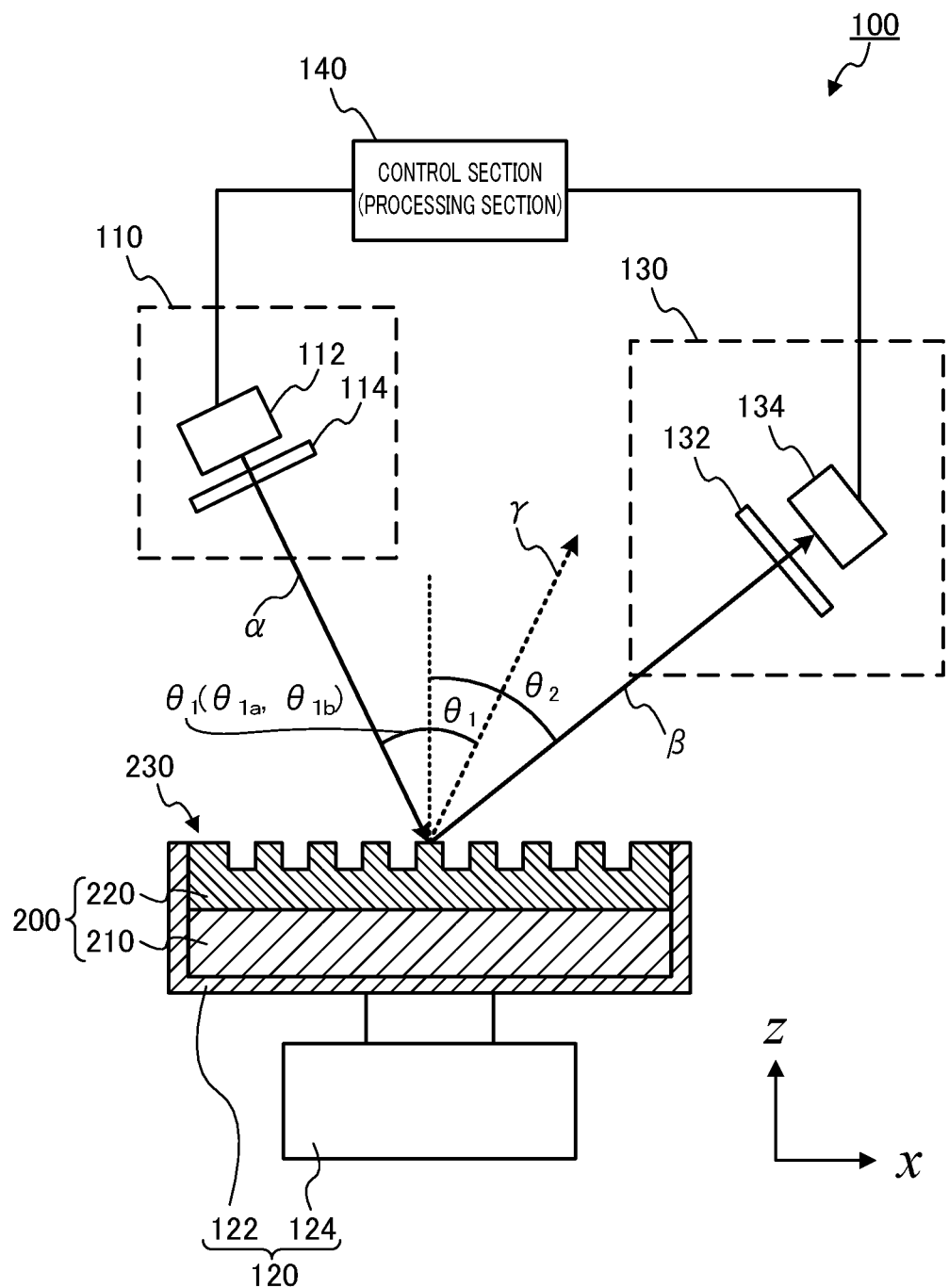
FIG. 1 is a schematic view illustrating a configuration of a surface plasmon-field enhanced fluorescence measurement apparatus (hereinafter referred to as "SPFS apparatus") according to Embodiment 1.

FIG. 1 is a schematic view illustrating a configuration of a surface plasmon-field enhanced fluorescence measurement apparatus (SPFS apparatus) 100 according to Embodiment 1 of the present invention.

As illustrated in FIG. 1, SPFS apparatus 100 includes excitation light irradiation unit 110, rotation section 120, fluorescence detection unit 130, and control section 140. SPFS apparatus 100 is used while chip 200 is mounted on chip holder 122 in rotation section 120. Detection chip 200 will be described first, followed by the description of SPFS apparatus 100.

(Configurations of Chip and SPFS Apparatus)

Chip 200 includes substrate 210 and metal film 220 formed on substrate 210. Diffraction grating 230 is formed in metal film 220. A ligand (e.g., primary antibody) is immobilized above diffraction grating 230, and a surface of diffraction grating 230 functions as a reaction site for binding a ligand and an analyte. In FIG. 1, a ligand and an analyte are not shown.

Substrate 210 is a support member for metal film 220. Materials for substrate 210 are not limited as long as they have enough mechanical strength to support metal film 220. Examples of the materials for substrate 210 include inorganic materials, such as glass, quartz, and silicon, and resins, such as polymethyl methacrylate, a polycarbonate, polystyrene, and a polyolefin.

Metal film 220 is disposed on substrate 210. As mentioned above, diffraction grating 230 is formed in metal film 220. Upon irradiation of metal film 220 with light, surface plasmon generated in metal film 220 and evanescent waves generated by diffraction grating 230 are coupled, thereby generating surface plasmon resonance.

Materials for metal film 220 are not limited as long as metals can generate surface plasmon. Examples of the materials for metal film 220 include gold, silver, copper, aluminum, and an alloy thereof. A formation method of metal film 220 is not limited. Examples of the formation methods of metal film 220 include sputtering, vapor deposition, and plating. The thickness of metal film 220 is not limited. The thickness of metal film 220 is, for example, 30 to 500 nm, preferably 100 to 300 nm.

Figure 2A:
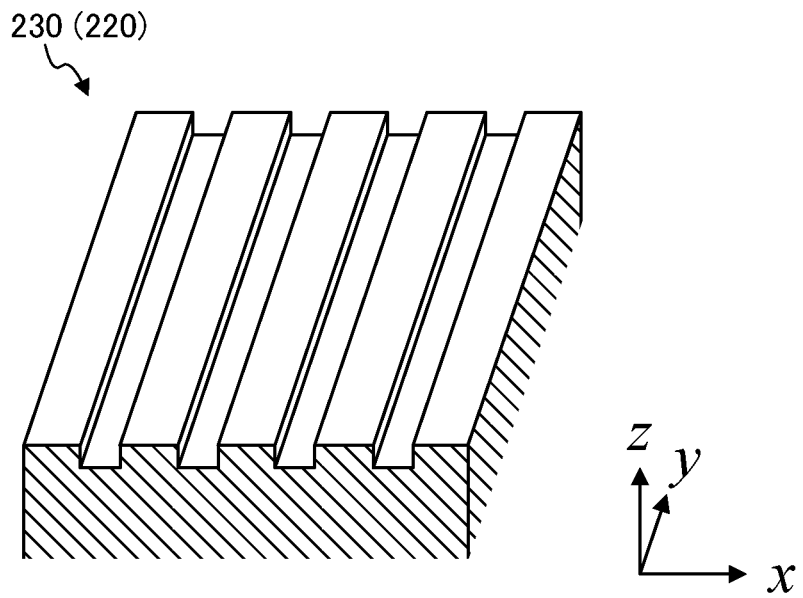
FIGS. 2A and 2B are perspective views of diffraction gratings.
Figure 2B:
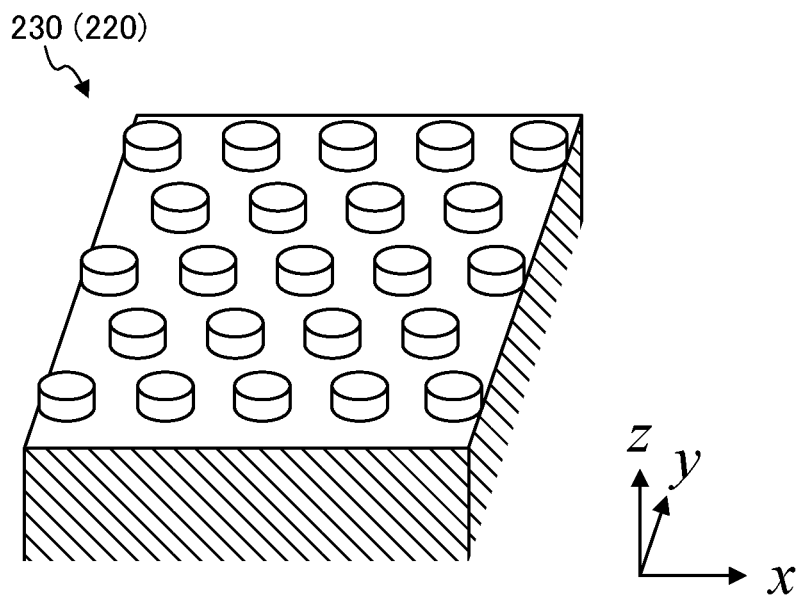

Diffraction grating 230 generates evanescent waves upon irradiation of metal film 220 with light. The shape of diffraction grating 230 is not limited as long as evanescent waves can be generated. For example, diffraction grating 230 may be a one-dimensional diffraction grating as illustrated in FIG. 2A, or may be a two-dimensional diffraction grating as illustrated in FIG. 2B. In the one-dimensional diffraction grating illustrated in FIG. 2A, a plurality of mutually parallel protruded strips (protruded portions extended in the surface direction of metal film 220) are formed at a predetermined pitch on a surface of metal film 220. In the two-dimensional diffraction grating illustrated in FIG. 2B, protruded portions of a predetermined shape are disposed periodically on a surface of metal film 220. Examples of the alignment of the protruded portions include a square lattice and a triangular (hexagonal) lattice. Examples of the cross-sectional shapes of diffraction grating 230 include a square waveform, a sinusoidal waveform, and a sawtooth shape.

A formation method of diffraction grating 230 is not limited. For example, after forming metal film 220 on planar substrate 210, protruded-recessed shapes may be imparted to metal film 220. Alternatively, metal film 220 may be formed on substrate 210 in which protruded-recessed shapes are imparted in advance. By either the method, metal film 220 including diffraction grating 230 can be formed.

A ligand for capturing an analyte is immobilized above diffraction grating 230 (reaction site). A ligand specifically binds to an analyte. In the embodiment, a ligand is almost evenly immobilized above a surface of diffraction grating 230. The type of ligand is not limited as long as an analyte can be captured. For example, a ligand is an antibody (e.g., primary antibody) specific to an analyte, a fragment thereof, or an enzyme that can specifically bonds to an analyte.

An immobilization method of a ligand is not limited. For example, a ligand-bound self-assembled monolayer (hereinafter referred to as "SAM") or polymer film may be formed above diffraction grating 230. Examples of SAM include films formed from a substituted aliphatic thiol, such as $HOOC(CH_2)_{11}SH$. Examples of component materials for the polymer film include polyethylene glycol and MPC polymer.

Alternatively, a polymer having a reactive group (or a functional group that can be converted into a reactive group) that can bind to a ligand may be immobilized above diffraction grating 230, followed by binding of a ligand to the polymer.

As illustrated in FIG. 1, metal film 220 (diffraction grating 230) is irradiated with excitation light α at predetermined incident angle $\theta_1$. In the irradiated region, surface plasmon generated in metal film 220 and evanescent waves generated by diffraction grating 230 are coupled, thereby generating SPR. When a fluorescent substance is present in the irradiated region, the fluorescent substance is excited by enhanced electric fields generated by SPR, and thus fluorescence β is emitted. In GC-SPFS, different from PC-SPFS, fluorescence β is emitted with directivity in a particular direction. For example, emission angle $\theta_2$ of fluorescence β is approximated as $2\theta_1$. Reflected light γ of excitation light α scarcely arises.

Figure 3A:
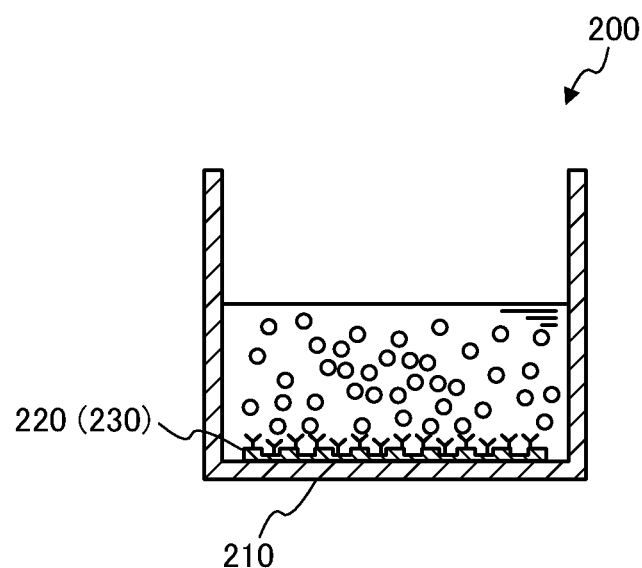
FIG. 3A is a schematic view illustrating a first mode of a chip according to Embodiment 1.
Figure 3B:
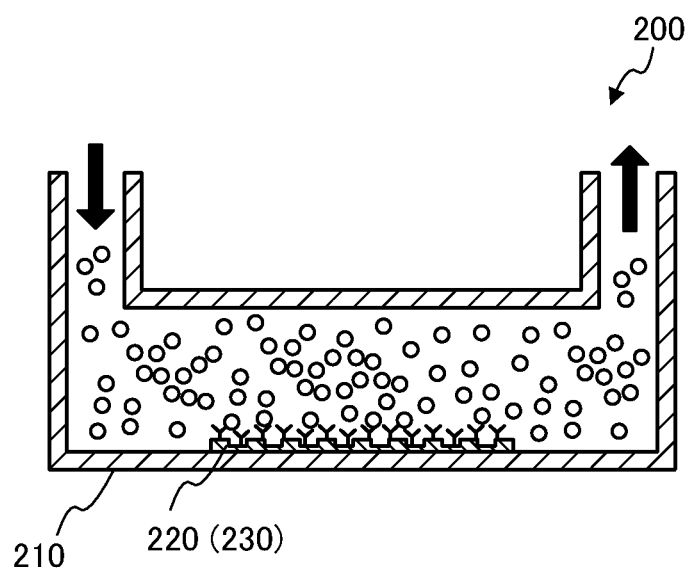
FIG. 3B is a schematic view illustrating a second mode of a chip according to Embodiment 1.

During use, diffraction grating 230 comes into contact with a liquid, such as a buffer, for a reaction, washing, or other operations. Accordingly, diffraction grating 230 is typically disposed in space where a liquid can be housed. As illustrated in FIG. 3A, for example, diffraction grating 230 may be disposed on an inner surface (e.g., bottom surface) of a well, which houses a liquid, or may be disposed on an inner surface (e.g., bottom surface) of a channel (flow cell), which can feed a liquid continuously, as illustrated in FIG. 3B. For example, detection chip 200 illustrated in FIG. 3A is suitable for a mass transfer analysis (real-time measurement) between the bulk and a surface of metal film 220, and a measurement of enhanced electric field space scale (z-axis direction), as well as a general measurement of an analyte (non-real-time measurement). For example, detection chip 200 illustrated in FIG. 3B is suitable for a reaction constant analysis (real-time measurement) of a molecule (analyte) relative to another molecule (ligand) immobilized above a surface of metal film 220, as well as a general measurement of an analyte (non-real-time measurement). The pitch of diffraction grating 230 is preferably about 400 nm, for example.

In the following, each component of SPFS apparatus 100 will be described. As mentioned above, SPFS apparatus 100 includes excitation light irradiation unit 110, rotation section 120, fluorescence detection unit 130, and control section 140.

Excitation light irradiation unit 110 irradiates metal film 220 (diffraction grating 230) of chip 200 with linearly polarized excitation light α having a certain wavelength and light quantity. In this step, excitation light irradiation unit 110 irradiates metal film 220 (diffraction grating 230) with linearly polarized excitation light α so as to generate, at diffraction grating 230, diffracted light that can couple with surface plasmon in metal film 220. In the embodiment, the optical axis of excitation light α is tilted from normal line N to metal film 220 in a side view of chip 200 (see FIG. 4A). Also, the optical axis of excitation light α is parallel to or tilted from straight line L along the alignment direction of a periodic structure of diffraction grating 230 (see FIG. 4B).

Excitation light irradiation unit 110 includes at least light source 112 and first polarizer 114. Excitation light irradiation unit 110 may further include a collimator lens, an excitation light filter, or the like.

Light source 112 emits excitation light α toward diffraction grating 230 of chip 200. In the embodiment, light source 112 is a laser diode. The type of light source 112 is not limited, and may not be a laser diode. Examples of light source 112 include a light emitting diode, a mercury lamp, and other laser light sources.

First polarizer 114 is disposed between light source 112 and diffraction grating 230, and isolates linearly polarized excitation light α from excitation light α emitted from light source 112. The type of first polarizer 114 is not limited as long as linearly polarized excitation light α with a predetermined polarization direction can be isolated. Examples of first polarizer 114 include a polarizing prism, a liquid crystal filter, and other polarizing filters. In the embodiment, first polarizer 114 is a polarizing plate. First polarizer 114 isolates linearly polarized excitation light α with an angle of an oscillation direction of the electric field in the range of 0±30° relative to a plane containing normal line N to a surface of metal film 220 and an optical axis of excitation light α (hereinafter referred to as "the plane") from excitation light α emitted from light source 112.

An excitation light filter (not shown) is disposed between light source 112 and chip 200, and modulates excitation light α emitted from light source 112. The excitation light filters include a bandpass filter, for example. Since excitation light α from a laser diode (light source 112) has some wavelength distribution widths, a bandpass filter converts excitation light α into narrow-band light solely composed of the central wavelength.

A collimator lens (not shown) is disposed between light source 112 and chip 200, and collimates excitation light α emitted from light source 112. Excitation light α emitted from a laser diode (light source 112) has a flat contour shape even after collimated. For this reason, the laser diode is held in a predetermined orientation so that the shape of an irradiation spot becomes almost circular on a surface of metal film 220. The size of the irradiation spot is preferably about 1 mm Ø, for example.

Incident angle $\theta_1$ of excitation light α on metal film 220 can be represented by incident angle $\theta_{1a}$ of excitation light α in a side view of chip 200 and incident angle $\theta_{1b}$ of excitation light α in a plan view of chip 200.

Figure 4A:
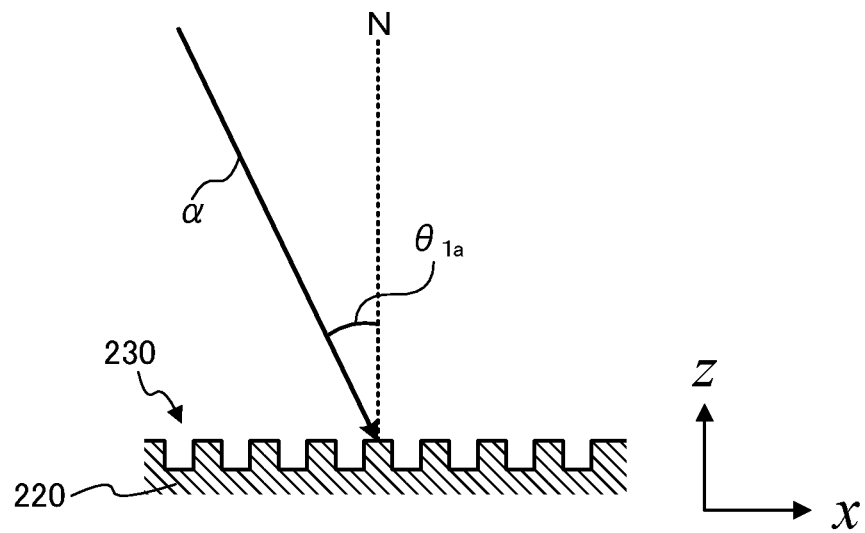
FIGS. 4A and 4B are schematic views for explaining an incident angle.
Figure 4B:
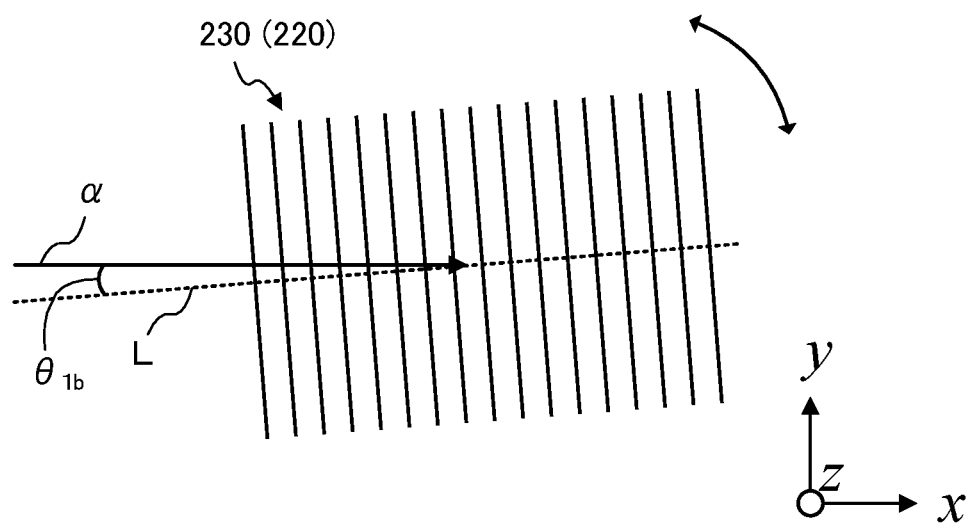

FIGS. 4A and 4B are schematic views for explaining an incident angle $\theta_1(\theta_{1a}, \theta_{1b})$. FIG. 4A is a schematic view for explaining incident angle $\theta_{1a}$ of excitation light α in a side view of chip 200, and FIG. 4B is a schematic view for explaining incident angle $\theta_{1b}$ of excitation light α in a plan view of chip 200. In the following description, x-axis direction is defined as an alignment direction of a periodic structure of diffraction grating 230, y-axis as an axis perpendicular to x-axis and parallel to a surface of metal film 220, and z-axis as an axis perpendicular to both x-axis and a surface of metal film 220.

As illustrated in FIG. 4A, the optical axis of excitation light α is tilted, by a predetermined angle, from normal line N to a surface of metal film 220 in a side view of chip 200. In a side view of chip 200, a small angle $\theta_{1a}$ (hereinafter also referred to as "incident angle $\theta_{1a}$ of excitation light α") between the optical axis of excitation light α and normal line N to a surface of metal film 220 is an angle at which fluorescence β (enhanced electric fields) becomes most intense. Incident angle $\theta_{1a}$ of excitation light α is appropriately selected in accordance with a pitch of diffraction grating 230, a wavelength of excitation light α, the type of a component metal for metal film 220, or the like. Since an optimal incident angle $\theta_{1a}$ of excitation light α in a side view of chip 200 varies in accordance with changes in various conditions, SPFS apparatus 100 preferably includes a first angle adjustment section (not shown) configured to adjust incident angle $\theta_{1a}$ by relatively rotating the optical axis of excitation light α and chip 200 around a straight line (as a central axis), which is positioned on a surface of metal film 220 and passes through an intersection between the optical axis of excitation light α and metal film 220 (diffraction grating 230). The first angle adjustment section, for example, may mutually rotate excitation light irradiation unit 110 and chip 200 around a straight line on a surface of metal film 220 passing through the intersection between the optical axis of excitation light α and metal film 220.

As illustrated in FIG. 4B, the optical axis of excitation light α is parallel to or tilted from straight line L along the alignment direction of a periodic structure of diffraction grating 230 (x-axis direction) in a plan view of chip 200. In a plan view of chip 200, a small angle $\theta_{1b}$ (hereinafter also referred to as "incident angle $\theta_{1b}$ of excitation light α") between the optical axis of excitation light α and straight line L along the alignment direction of a periodic structure of diffraction grating 230 is an angle at which a difference value between a detected value of a first light (e.g., light with an angle of an oscillation direction of the electric field of 0° relative to the plane) and a detected value of a second light (e.g., light with an angle of an oscillation direction of the electric field of 90° relative to the plane) becomes zero when a liquid containing a fluorescent substance is present on metal film 220 described below. An adjustment method of incident angle $\theta_{1b}$ of excitation light α in a plan view of chip 200 is not limited. In the embodiment, incident angle $\theta_{1b}$ of excitation light α in a plan view of chip 200 is adjusted by rotation section 120. For achieving the most intense fluorescence β (enhanced electric fields), an optimal incident angle $\theta_1$ in a plan view of chip 200 requires the optical axis of excitation light α to be extended along the alignment direction of a periodic structure of diffraction grating 230 (x-axis direction in FIGS. 2A and 2B). In order to measure an analyte more accurately, the embodiment sets an angle of the optical axis of excitation light α relative to straight line L along the alignment direction of a periodic structure of diffraction grating 230.

Rotation section 120 changes an optical axis direction (angle) of excitation light α relative to diffraction grating 230 in a plan view. In the embodiment, rotation section 120 rotates diffraction grating 230 (chip 200) around normal line N (to a surface of metal film 220) passing through an intersection between the optical axis of excitation light α and metal film 220 as a central axis.

The configuration of rotation section 120 is not limited as long as an optical axis direction of excitation light α relative to diffraction grating 230 in a plan view can be changed. For example, rotation section 120 includes chip holder 122 and motor 124. The configuration of chip holder 122 is not limited as long as chip 200 can be held. In the embodiment, chip holder 122 is formed as a box with the top surface opened so that chip 200 can be housed inside. Motor 124 rotates chip holder 122 around normal line N as a central axis. Motor 124 is connected to a chip holder 122, and thus chip 200 is rotated by a predetermined angle by rotating motor 124.

Fluorescence detection unit 130 is disposed facing excitation light irradiation unit with normal line N (to a surface of metal film 220 passing through an intersection between the optical axis of excitation light α and metal film 220) therebetween. Fluorescence detection unit 130 detects reflected light γ (of excitation light α) reflected on metal film 220 and fluorescence β emitted from a fluorescent substance above diffraction grating 230 (reaction site).

Fluorescence detection unit 130 includes at least second polarizer 132 and light detection section 134. Fluorescence detection unit 130 may further include a condensing lens group, an aperture stop, a fluorescence filter, or the like.

Second polarizer 132 is disposed between diffraction grating 230 and light detection section 134, and isolates linearly polarized light from fluorescence β emitted from a fluorescent substance. The type of second polarizer 132 is not limited as long as linearly polarized light with a predetermined polarization direction can be isolated. Examples of second polarizer 132 include a polarizing prism, a liquid crystal filter, and other polarizing filters. In the embodiment, second polarizer 132 is a polarizing plate. Second polarizer 132 is held so that it can rotate in a plane perpendicular to the propagation direction of fluorescence β toward light detection section 134 from metal film 220.

Second polarizer 132 isolates two types of light during determination of incident angle $\theta_{1b}$ of excitation light α in a plan view of chip 200 and during detection of an analyte. During determination of incident angle $\theta_{1b}$ of excitation light α, second polarizer 132 isolates, from fluorescence β emitted from a fluorescent substance when a liquid containing the fluorescent substance is present on metal film 220, first light with an angle of an oscillation direction of the electric field in the range of 0±30° relative to the plane and second light with an angle of an oscillation direction of the electric field in the range of 90±30° relative to the plane. Preferably, second polarizer 132 isolates, from fluorescence β, light with an angle of an oscillation direction of the electric field of 0° relative to the plane as a first light and light with an angle of an oscillation direction of the electric field of 90° relative to the plane as a second light.

During detection of an analyte, second polarizer 132 isolates, from fluorescence β emitted from a fluorescent substance when an analyte labeled with the fluorescent substance is captured by a ligand, third light with an angle of an oscillation direction of the electric field in the range of 0±30° relative to the plane and fourth light with an angle of an oscillation direction of the electric field in the range of 90±30° relative to the plane. Preferably, second polarizer 132 isolates, from fluorescence β, light with an angle of an oscillation direction of the electric field of 0° relative to the plane as a third light and light with an angle of an oscillation direction of the electric field of 90° relative to the plane as a fourth light.

In the embodiment, the first light or the second light is isolated by rotating second polarizer (polarizing plate) 132. Also, the third light or the fourth light is isolated by rotating second polarizer (polarizing plate) 132.

Light detection section 134 detects linearly polarized light isolated by second polarizer 132 to detect a fluorescence image above metal film 220. When second polarizer 132 isolates the first light or the second light from fluorescence β, light detection section 134 detects the first light or the second light. When second polarizer 132 isolates the third light or the fourth light from fluorescence β, light detection section 134 detects the third light or the fourth light. Light detection section 134 is, for example, a photomultiplier tube with high sensitivity and a high S/N ratio. Light detection section 134 may be an avalanche photodiode (APD), a photodiode (PD), a CCD image sensor, or the like.

A condensing lens group (not shown) is disposed between chip 200 and light detection section 134, and constitutes a conjugate optical system insusceptible to stray light. A condensing lens group images, on light receiving surface of light detection section 134, a fluorescence image above metal film 220.

A fluorescence filter (not shown) is disposed between chip 200 and light detection section 134. For example, the fluorescence filters, which include a cutoff filter and a neutral density (ND) filter, eliminate noise component (e.g., excitation light α and extraneous light), which is light that reaches light detection section 134 excluding fluorescence β, and adjust light quantity of light that reaches light detection section 134.

As mentioned above, in GC-SPFS, fluorescence β is emitted from diffraction grating 230 (reaction site) with directivity in a particular direction. Accordingly, an optical axis angle of fluorescence detection unit 130 relative to normal line N to a surface of metal film 220 is preferably an angle at which the intensity of fluorescence β is maximum (fluorescence peak angle). Thus, SPFS apparatus 100 preferably includes a second angle adjustment section (not shown) configured to adjust an optical axis angle of fluorescence detection unit 130 by relatively rotating the optical axis of fluorescence detection unit 130 and chip 200. For example, the second angle adjustment section may mutually rotate fluorescence detection unit 130 and chip 200 around a straight line on a surface of metal film 220 passing through an intersection between the optical axis of fluorescence detection unit 130 and metal film 220.

Control section 140 controls the operations of excitation light irradiation unit 110 (light source 112, first polarizer 114, and first angle adjustment section), rotation section 120 (motor 124), and fluorescence detection unit 130 (second polarizer 132, light detection section 134, and second angle adjustment section). Control section 140 also functions as a processing section that processes output signals (detected results) from light detection section 134. Control section 140 is a computer that executes software, for example.

(Surface Plasmon-Field Enhanced Fluorescence Measurement Method)

Figure 5:
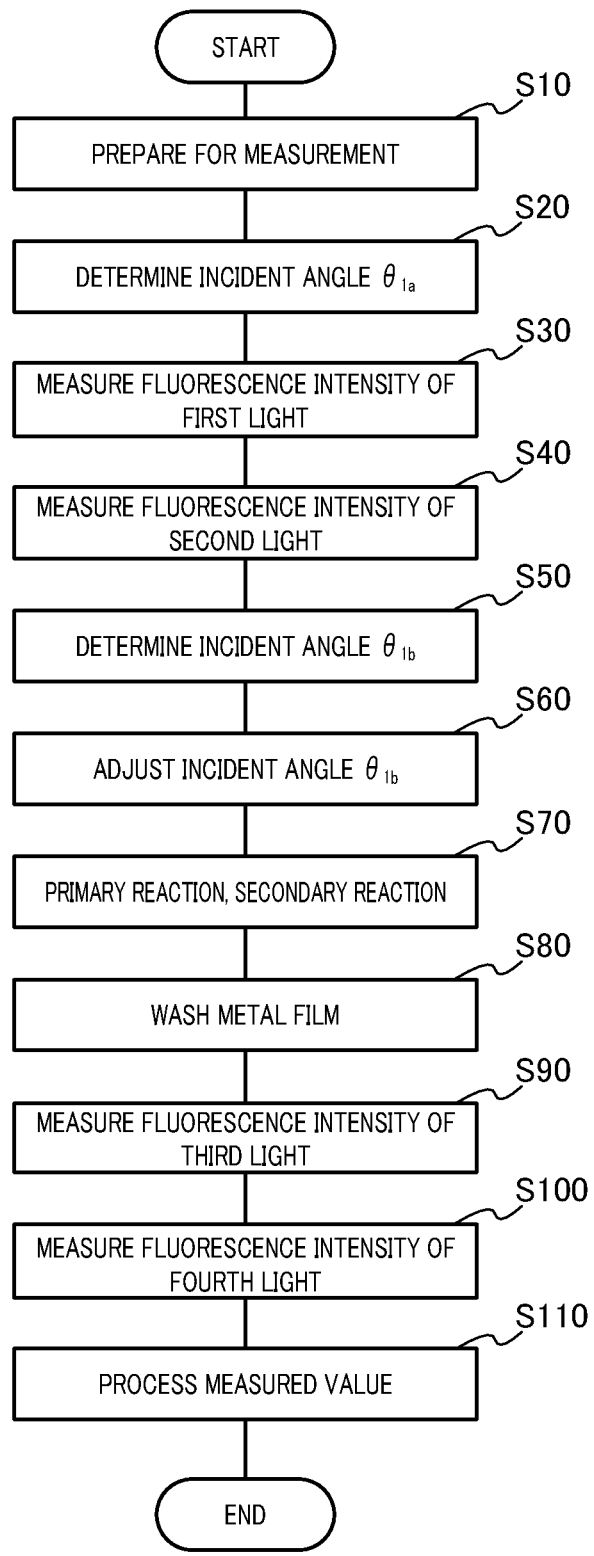
FIG. 5 is a flow chart showing the operations of a SPFS apparatus according to Embodiment 1.
Figure 6A:
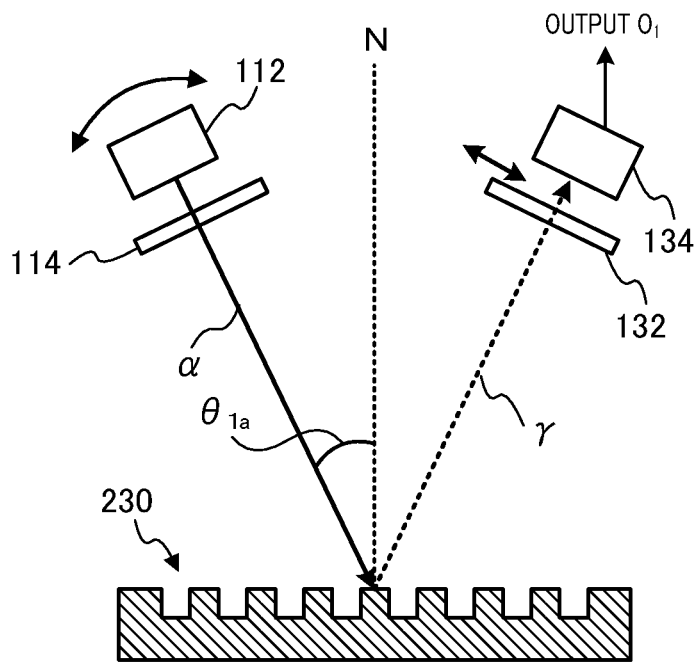
FIGS. 6A and 6B are schematic views illustrating a measurement procedure of fluorescence intensity.
Figure 6B:
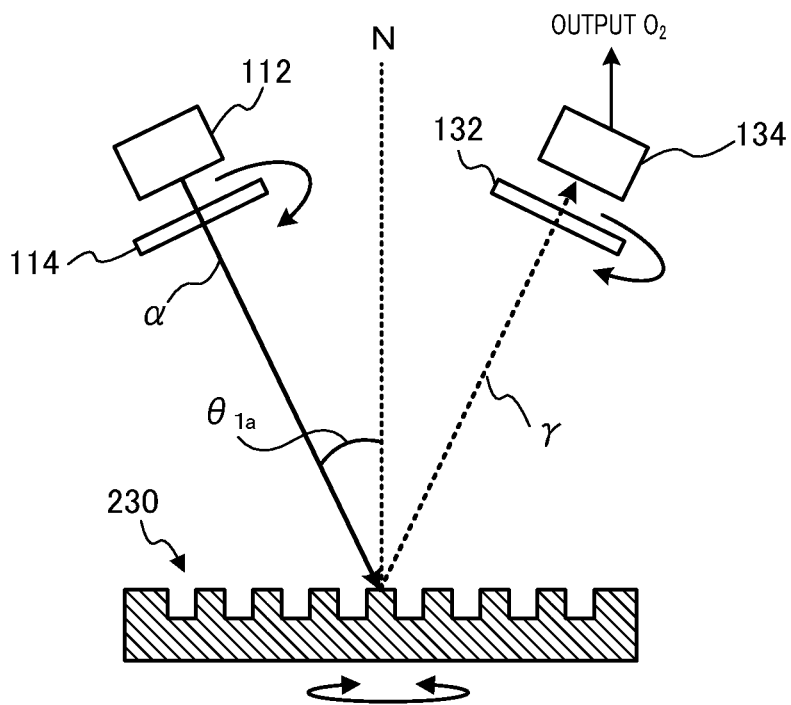
Figure 7A:
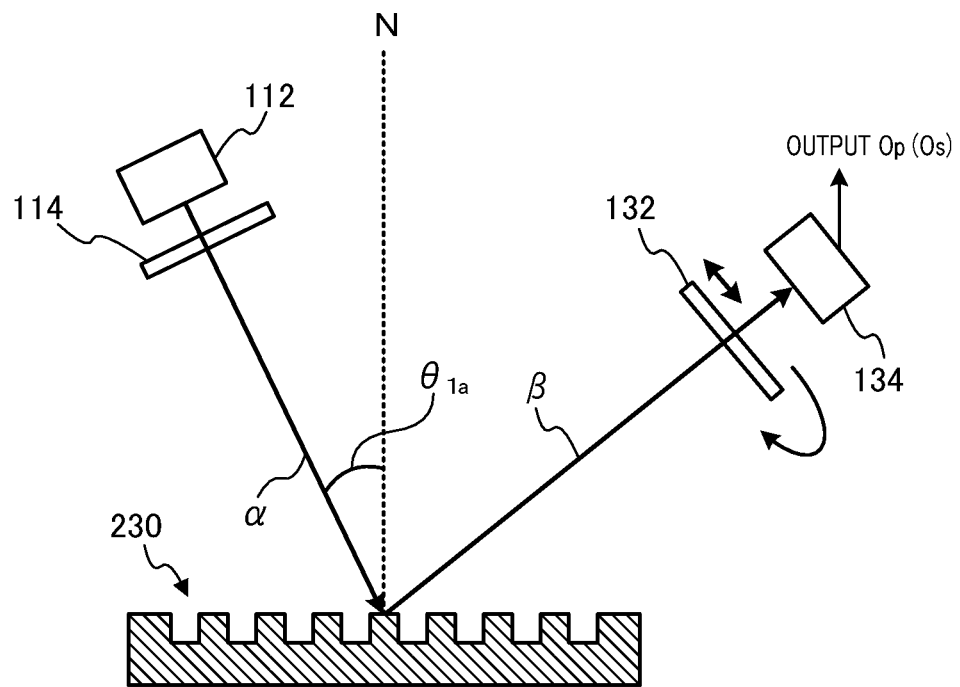
FIG. 7A is a schematic view illustrating a measurement procedure of fluorescence intensity.
Figure 7B:
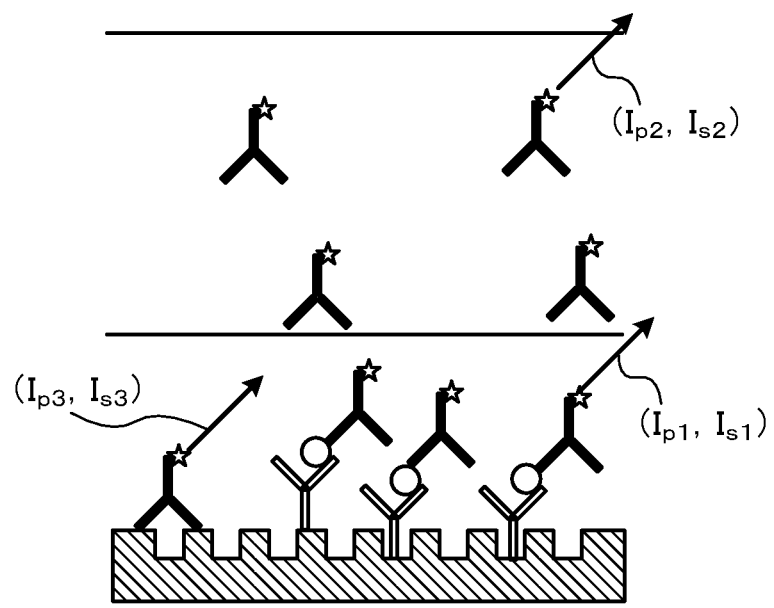
FIG. 7B is a view for explaining a measurement principle.

In the following, the detection operations of SPFS apparatus 100 (surface plasmon-field enhanced fluorescence measurement method) will be described. FIG. 5 is a flow chart showing an example of an operational procedure of SPFS apparatus 100. FIGS. 6A, 6B, and 7A are schematic views illustrating a measurement procedure of fluorescence intensity. FIG. 7B is a view for explaining a measurement principle. In this example, a primary antibody as a ligand is immobilized above metal film 220. As a ligand for fluorescent labeling, a secondary antibody labeled with a fluorescent substance is used.

First, the measurement is prepared (step S10). Specifically, chip 200 is prepared, and then chip 200 is installed in chip holder 122. When a humectant is present above/on metal film 220 of chip 200, the humectant is removed by washing above/on metal film 220 so that a primary antibody properly captures an analyte.

Control section 140 then determines incident angle $\theta_{1a}$ of excitation light α in a side view of chip 200 (step S20). Specifically, as illustrated in FIG. 6A, control section 140 irradiates a predetermined position of metal film 220 with excitation light α while a first angle adjustment section scans over incident angle $\theta_{1a}$ of excitation light α on metal film 220. Control section 140 also controls a second angle adjustment section so that light detection section 134 detects reflected light γ from above metal film 220. Reflected light γ of excitation light α reflected on metal film 220 reaches light detection section 134. Thus, control section 140 obtains data containing a relationship between incident angle $\theta_{1a}$ of excitation light α and light quantity of reflected light γ (of excitation light α). After that, control section 140 analyzes the data and determines incident angle $\theta_{1a}$ at which light quantity of reflected light γ (of excitation light α) becomes minimum. During this step, incident angle $\theta_{1b}$ of excitation light α is set to 0°. Meanwhile, first polarizer 114 and second polarizer 132 may not be disposed on the optical path of excitation light α and the optical path of reflected light γ, respectively.

The determined incident angle $\theta_{1a}$ of excitation light α in a side view of chip 200 is an angle at which light quantity of reflected light γ (of excitation light α) becomes minimum. Thus, when incident angle $\theta_{1b}$ of excitation light α is set to 0° in a plan view of chip 200, incident angle $\theta_1$ ($\theta_{1a}$, $\theta_{1b}$) of excitation light α is a resonance angle. In GC-SPFS, a resonance angle at which light quantity of reflected light γ (of excitation light α) becomes minimum, and an enhanced angle at which the intensity of enhanced electric fields become highest are almost the same value. In other words, when incident angle $\theta_{1b}$ of excitation light α is set to 0°, a resonance angle and an enhanced angle can be obtained by obtaining incident angle $\theta_1$ ($\theta_{1a}$, $\theta_{1b}$) of excitation light α at which light quantity of reflected light γ (of excitation light α) becomes minimum. The determined incident angle $\theta_{1a}$ is used for a measurement of an analyte.

Then, the fluorescence intensity of a first light is measured (step S30). Specifically, a fluorescent labeling solution containing a secondary antibody labeled with a fluorescent substance is provided first. Thus, a measurement of the fluorescence intensity of the first light is performed while a liquid containing a fluorescent substance is present on metal film 220. Then, as illustrated in FIG. 6B, control section 140 operates light source 112 to irradiate a predetermined position of metal film 220 with excitation light α, and simultaneously drives motor 124 in rotation section 120 to scan over an optical axis direction (incident angle $\theta_{1b}$) of excitation light α relative to a periodic direction of diffraction grating 230 of metal film 220 (chip 200 is rotated in the horizontal direction). In this step, incident angle $\theta_{1a}$ is the angle determined in step S20 at which light quantity of reflected light γ becomes minimum. Control section 140 also adjusts a rotation angle of second polarizer 132 so that only the first light contained in fluorescence β (e.g., light with an angle of an oscillation direction of the electric field of 0° relative to the plane) can be transmitted through. Light detection section 134 outputs a measured result (output $O_1$) to control section (processing section) 140. Output $O_1$ is the fluorescence intensity of the first light of fluorescence β emitted from a suspended fluorescent substance above metal film 220 (noise component).

In step S30, a liquid containing only a fluorescent substance may be provided. In this case, a sample is first provided to react an analyte in a sample with a primary antibody (primary reaction), and then, a secondary antibody is provided to react the analyte with the secondary antibody while reacting the secondary antibody with a fluorescent substance (secondary reaction) in step S70 described hereinafter.

Then, the fluorescence intensity of a second light is measured (step S40). Specifically, as illustrated in FIG. 6B, control section 140 operates light source 112 to irradiate a predetermined position of metal film 220 with excitation light α, and simultaneously drives motor 124 in rotation section 120 to scan over an optical axis direction (incident angle $θ_{1b}$) of excitation light α relative to a periodic direction of diffraction grating 230 of metal film 220. In this step, incident angle $θ_{1b}$ is the same angle as in step S30. Control section 140 also adjusts a rotation angle of second polarizer 132 so that only the second light contained in fluorescence β (e.g., light with an angle of an oscillation direction of the electric field of 90° relative to the plane) can be transmitted through. Light detection section 134 outputs a measured result (output $O_2$) to control section (processing section) 140. Output $O_2$ is the fluorescence intensity of the second light of fluorescence β emitted from a suspended fluorescent substance above metal film 220 (noise component).

The order of the measurement of the fluorescence intensity of the first light (step S30) and the measurement of the fluorescence intensity of the second light (step S40) is not limited to the aforementioned one. For example, the fluorescence intensity of the first light may be measured after measuring the fluorescence intensity of the second light.

Next, control section 140 determines incident angle $θ_{1b}$ (step S50). Specifically, control section 140 obtains an angle at which a difference value between the fluorescence intensity of the first light and the fluorescence intensity of the second light becomes zero from the measured results (output $O_1$ and output $O_2$) obtained in step S30 and step S40. Control section 140 determines an angle at which a difference value between the fluorescence intensity of the first light and the fluorescence intensity of the second light becomes zero as incident angle $θ_{1b}$.

As mentioned above, incident angle $θ_{1b}$ is an angle at which a difference value between the fluorescence intensity of the first light (noise component) and the fluorescence intensity of the second light (noise component) becomes zero. By setting incident angle $θ_{1b}$ so that a difference value between the fluorescence intensity of the first light and the fluorescence intensity of the second light becomes zero, the fluorescence intensity of a suspended fluorescent substance and a difference value between the fluorescence intensity of the first light and the fluorescence intensity of the second light can be cancelled in step S110 described hereinafter.

Then, Control section 140 adjusts incident angle $θ_{1b}$ of excitation light α in a plan view of chip 200 (step S60). Specifically, control section 140 rotates diffraction grating (chip 200) so that an optical axis angle of excitation light α relative to a periodic direction of diffraction grating 230 of metal film 220 becomes incident angle $θ_{1b}$ obtained in step S 50.

After that, control section 140 reacts an analyte in a sample with a primary antibody while reacting the analyte with a labeled secondary antibody (primary reaction, secondary reaction: step S70). Specifically, a sample is provided on metal film 220 so that the sample comes into contact with the primary antibody. When the analyte is present in the sample, at least part of the analyte binds to the primary antibody. When the analyte is bound to the primary antibody, at least part of the analyte binds to the secondary antibody which is already present, thereby being labeled with a fluorescent substance. The types of sample and analyte are not limited. Examples of the samples include bodily fluids, such as blood, serum, plasma, urine, nostril mucus, saliva, and semen, and dilute solutions thereof. Examples of analytes include a nucleic acid (DNA, RNA, or the like), a protein (a polypeptide, an oligopeptide, or the like), an amino acid, a carbohydrate, a lipid, and a modified molecule thereof.

As an optional step, metal film 220 is washed (step S80). Specifically, it is preferable to wash above/on metal film 220 with a buffer to remove a free secondary antibody or the like after labeling with the fluorescent substance. Even when metal film 220 is washed by replacing a fluorescent labeling solution above/on metal film 220 with a secondary antibody-free buffer after the primary reaction and the secondary reaction (step S70), part of the secondary antibody bound to the analyte is released in the buffer. Meanwhile, when washing is not performed after the primary reaction and the secondary reaction (step S70), the fluorescent labeling solution is left untouched above/on metal film 220. In this case, real-time measurements are possible, and there is an advantage that a low-affinity substance, which cannot be measured if washing is performed, can become a measurement target. Also, by eliminating a washing step, the measurement time can be shortened.

Then, the fluorescence intensity of a third light is measured (a measurement of the analyte) (step S90). Specifically, control section 140 operates light source 112 to emit excitation light α. At the same time, control section 140 operates light detection section 134 to detect the intensity of fluorescence β from metal film 220. In this case, incident angle $θ_{1b}$ of excitation light α is the angle determined in step S20, and incident angle $θ_{1b}$ is the angle determined in step S50. As illustrated in FIG. 7A, control section 140 adjusts an rotation angle of second polarizer 132 so that only the third light contained in fluorescence β (in the figure, light with an angle of an oscillation direction of the electric field of 0° relative to the plane) can be transmitted through. Light detection section 134 outputs a measured result (output Op) to control section (processing section) 140. Output Op contains a signal component and at least part of the fluorescent intensity of the first light.

In GC-SPFS, fluorescence β (signal component) emitted from a fluorescent substance that labels an analyte is light with an angle of an oscillation direction of the electric field of 0° relative to the plane or light close to light with an angle of an oscillation direction of the electric field of 0° relative to the plane. Such fluorescence β passes through second polarizer 132 to reach light detection section 134. Also, the first light contained in fluorescence β of a suspended fluorescent substance reaches light detection section 134. As a result, the measured result in this step (output Op) contains a signal component and at least part of the fluorescence intensity of the first light.

Then, the fluorescence intensity of a fourth light is measured (a measurement of the analyte) (step S100). Specifically, control section 140 operates light source 112 to emit excitation light α. At the same time, control section 140 operates light detection section 134 to detect the intensity of fluorescence β from metal film 220. As illustrated in FIG. 7A, control section 140 adjusts an rotation angle of second polarizer 132 so that only the fourth light contained in fluorescence β (in the figure, light with an angle of an oscillation direction of the electric field of 90° relative to the plane) can be transmitted through. Light detection section 134 outputs a measured result (output Os) to control section (processing section) 140. Since fluorescence β emitted from a fluorescent substance that labels an analyte (signal component) scarcely contains light with an angle of an oscillation direction of the electric field of 90° relative to the plane or light close to light with an angle of an oscillation direction of the electric field of 90°, output Os is primarily composed of at least part of the fluorescence intensity of the second light.

The order of the measurement of the fluorescence intensity of the third light (step S90) and the measurement of the fluorescence intensity of the fourth light (step S100) is not limited to the aforementioned one. For example, the intensity of the third light may be measured after measuring the intensity of the fourth light.

Finally, control section (processing section) 140 analyzes output signals (outputs Op and Os) from light detection section 134, and analyzes the presence of the analyte or an amount of the analyte (step S110). Specifically, control section (processing section) 140 calculates a difference value between output Op and output Os to obtain a signal value.

In the following, a measurement principle of surface plasmon-field enhanced fluorescence measurement method will be described with reference to FIG. 7B. In FIG. 7B, $I_{p1}$ denotes a component of light, of fluorescence β emitted from a fluorescent substance that labels an analyte, having an angle of an oscillation direction of the electric field of 0° relative to the plane, whereas $I_{s1}$ denotes a component of light, of fluorescence β emitted from a fluorescent substance that labels an analyte, having an angle of an oscillation direction of the electric field of 90° relative to the plane. $I_{p2}$ denotes a component of light, of fluorescence β emitted from a suspended fluorescent substance positioned in space where enhanced electric fields are not exerted, having an angle of an oscillation direction of the electric field of 0° relative to the plane, whereas $I_{s2}$ denotes a component of light, of fluorescence β emitted from a suspended fluorescent substance positioned in space where enhanced electric fields are not exerted, having an angle of an oscillation direction of the electric field of 90° relative to the plane. $I_{p3}$ denotes a component of light, of fluorescence β emitted from a fluorescent substance nonspecifically adhered to metal film 220, having an angle of an oscillation direction of the electric field of 0° relative to the plane, whereas $I_{s3}$ denotes a component of light, of fluorescence β emitted from a fluorescent substance nonspecifically adhered to metal film 220, having an angle of an oscillation direction of the electric field of 90° relative to the plane. In FIG. 7B, the white circles represent an analyte, the white Y-shaped structures represent a ligand (primary antibody), the black inverted Y-shaped structures represent a secondary antibody, and the white stars represent a fluorescent substance.

As illustrated in FIG. 7B, during measurement of the analyte (measurement of the fluorescence intensity of the third light; step S90), light component $I_p$ of fluorescence β with an angle of an oscillation direction of the electric field of 0° relative to the plane is represented by equation 1.

$$I_p = I_{p1} + I_{p2} + I_{p3} \tag{Equation 1}$$

During measurement of the analyte (measurement of the fluorescence intensity of the fourth light; step S100), light component $I_s$ of fluorescence β with an angle of an oscillation direction of the electric field of 90° relative to the plane is represented by equation 2.

$$I_s = I_{s1} + I_{s2} + I_{s3} \tag{Equation 2}$$

Further, as represented by equation 3, a difference value between light component $I_p$ of fluorescence β having an angle of an oscillation direction of the electric field of 0° relative to the plane and light component $I_s$ of fluorescence β having an angle of an oscillation direction of the electric field of 90° relative to the plane can be obtained by subtracting equation 2 from equation 1.

$$I_p - I_s = (I_{p1} - I_{s1}) + (I_{p2} - I_{s2}) + (I_{p3} - I_{s3}) \tag{Equation 3}$$

A fluorescent substance excited by enhanced electric fields scarcely emit light with an angle of an oscillation direction of the electric field of 90° relative to the plane and light close to light with an angle of an oscillation direction of the electric field of 90° relative to the plane. Thus, light components ($I_{s1}$) and ($I_{s3}$), of fluorescence β emitted from a fluorescent substance present in a region where enhanced electric fields are exerted, having an angle of an oscillation direction of the electric field of 90° relative to the plane can be approximated to zero. Accordingly, the aforementioned equation 3 becomes equation 4.

$$I_p - I_s = I_{p1} + (I_{p2} - I_{s2}) + I_{p3} \tag{Equation 4}$$

Meanwhile, the second term of "$I_{p2} - I_{s2}$" in the right-hand side is a difference value between a light component, of fluorescence β emitted from a suspended fluorescent substance positioned in space where enhanced electric fields are not exerted, having an angle of an oscillation direction of the electric field of 0° relative to the plane, and a light component, of fluorescence β emitted from a suspended fluorescent substance positioned in space where enhanced electric fields are not exerted, having an angle of an oscillation direction of the electric field of 90° relative to the plane. The embodiment is set to "$I_{p2} - I_{s2} = 0$" (see step S30 to step S50). Thus, the aforementioned equation 4 becomes equation 5.

$$I_p - I_s = I_{p1} + I_{p3} \tag{Equation 5}$$

Further, a light component ($I_{p3}$), of fluorescence β emitted from a fluorescent substance nonspecifically adhered to metal film 220, having an angle of an oscillation direction of the electric field of 0° relative to the plane is an extremely small value compared with a light component ($I_{p1}$), of fluorescence β emitted from a fluorescent substance that labels an analyte, having an angle of the oscillation direction of the electric field of 0° relative to the plane, and thus is approximated to zero. Thus, the aforementioned equation 5 becomes equation 6.

$$I_p - I_s = I_{p1} \tag{Equation 6}$$

As in the foregoing, surface plasmon-field enhanced fluorescence measurement method according to the embodiment, which satisfies "$I_{p2} - I_{s2} = 0$", can detect the fluorescence intensity of fluorescence β emitted from a fluorescent substance that labels an analyte even when the fluorescence intensity of the first light and the fluorescence intensity of the second light are different values.

Through the above procedure, the presence of an analyte or an amount of an analyte in a sample can be detected.

Therefore, SPFS apparatus 100 of the embodiment can detect an analyte with higher sensitivity than conventional SPFS apparatuses, since only a signal component can be detected utilizing the difference in polarization characteristics between a signal component and a noise component.

Moreover, since SPFS apparatus 100 of the embodiment can remove a noise component contained in fluorescence β, an analyte can be detected without removal of a free secondary antibody (washing of metal film 220; step S80) after performing the primary reaction and the secondary reaction (step S70).

In the aforementioned embodiment, although diffraction grating 230 (chip 200) is rotated around normal line N to metal film 220 as a rotational axis, the optical axis of excitation light α may be rotated relative to diffraction grating 230 (chip 200).

In the aforementioned embodiment, although an example of irradiating chip 200 with excitation light α from the side of metal film 220 is described, chip 200 may be irradiated with excitation light α from the side of substrate 210.

Embodiment 2

SPFS apparatus 300 according to Embodiment 2 is different from SPFS apparatus 100 according to Embodiment 1 in that the configuration of rotation section 320 differs from that of rotation section 120. Thus, the configuration of rotation section 320 will be primarily described. The same components as those of SPFS apparatus 100 are denoted by the same numerals, and thus their descriptions will be omitted. Chip 200 is the same as chip 200 according to Embodiment 1, and thus the description will be omitted.

(Configuration of SPFS Apparatus)

Figure 8:
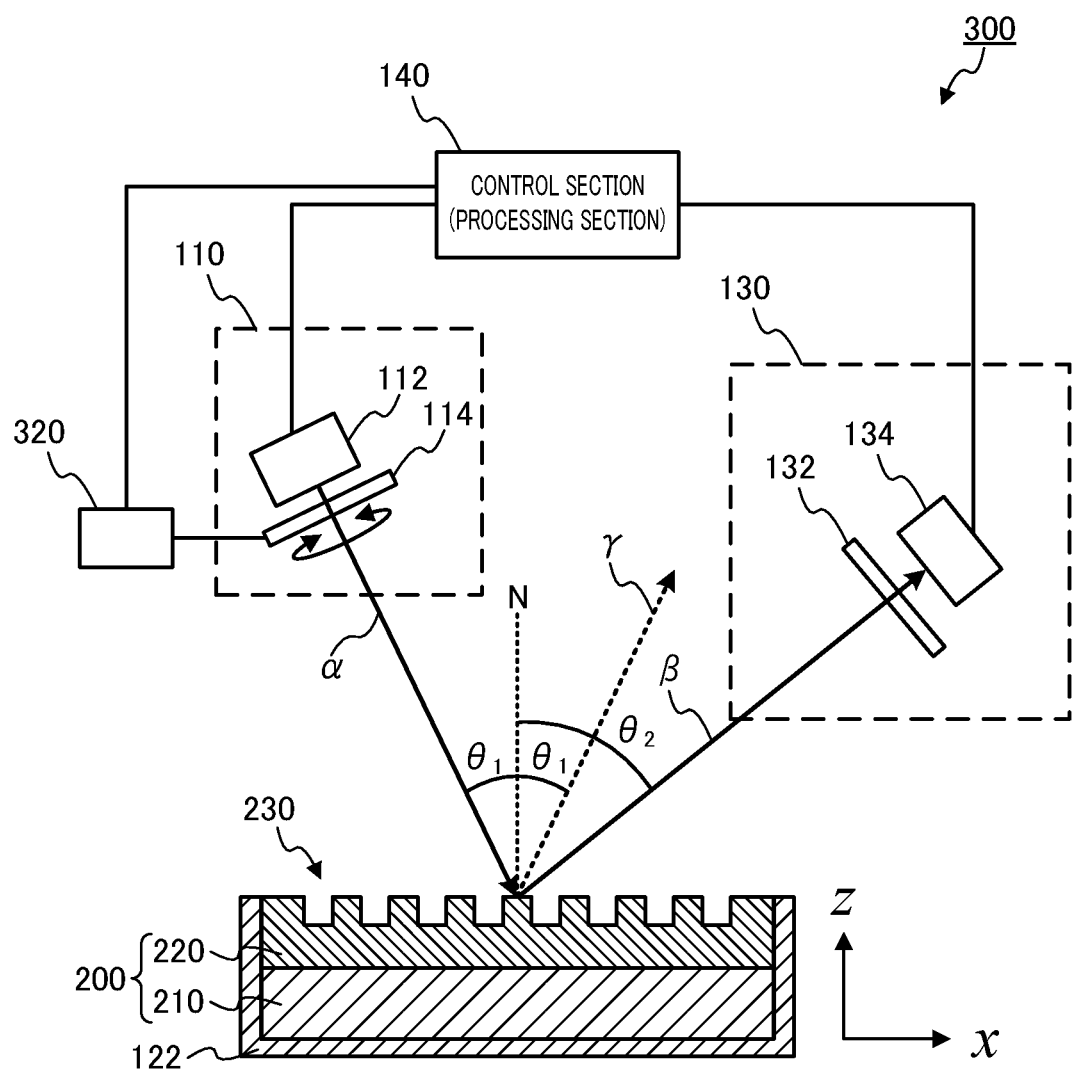
FIG. 8 is a schematic view illustrating a configuration of a SPFS apparatus according to Embodiment 2.

FIG. 8 is a schematic view illustrating a configuration of SPFS apparatus 300 according to Embodiment 2. As illustrated in FIG. 8, SPFS apparatus 300 according to Embodiment 2 includes excitation light irradiation unit 110, rotation section 320, fluorescence detection unit 130, and control section 140.

Rotation section 320 changes the polarization direction of excitation light α relative to diffraction grating 230. Rotation section 320 is connected to first polarizer 114, and rotates first polarizer 114 around the optical axis of excitation light α as a central axis. By rotating first polarizer 114, the polarization direction of linearly polarized excitation light α is rotated.

(Surface Plasmon-Field Enhanced Fluorescence Measurement Method)

Figure 9:
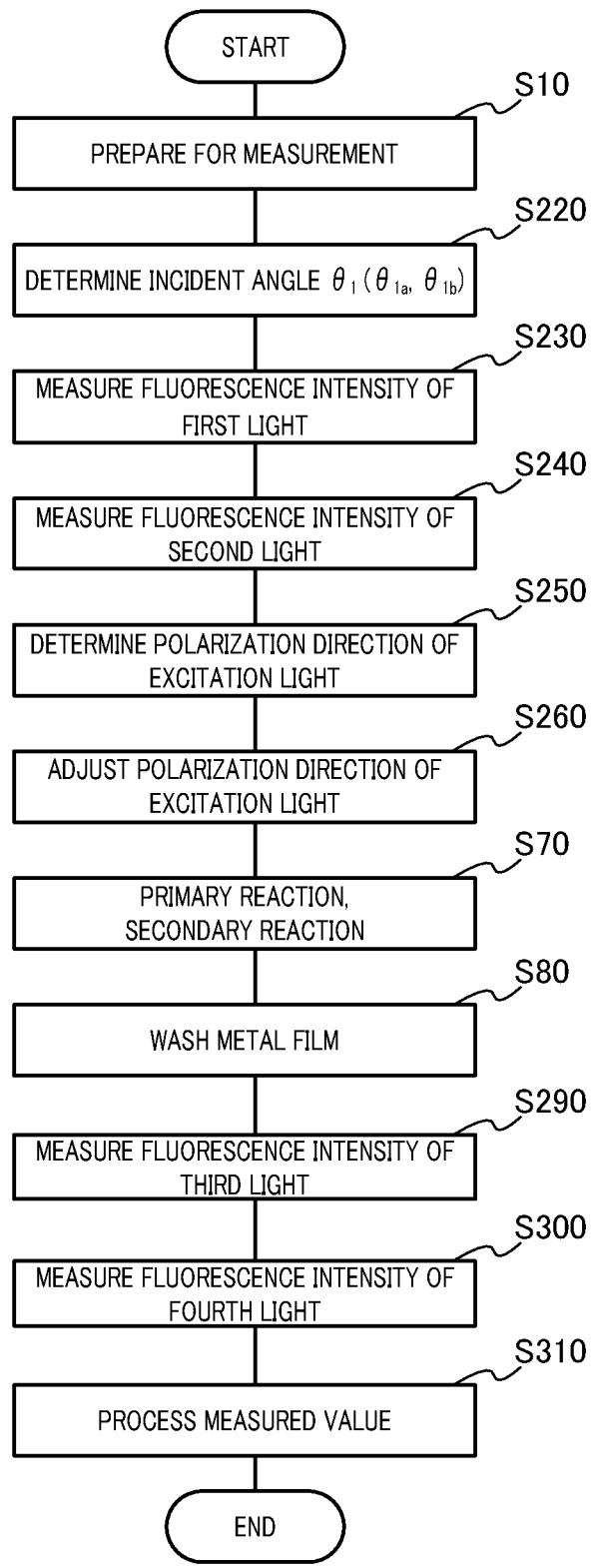
FIG. 9 is a flow chart showing the operations of a SPFS apparatus according to Embodiment 2.

In the following, the detection operations of SPFS apparatus 300 (surface plasmon-field enhanced fluorescence measurement method) will be described. FIG. 9 is a flow chart showing an example of an operational procedure of SPFS apparatus 300. The same steps as those in the detection operations of SPFS apparatus 100 according to Embodiment 1 are denoted by the same numerals, and thus their detailed descriptions will be omitted.

First, the measurement is prepared (step S10).

Then, incident angle $\theta_1$ ($\theta_{1a}$, $\theta_{1b}$) of excitation light α is determined (step S220). Specifically, control section 140 irradiates a predetermined position of metal film 220 with excitation light α while a first angle adjustment section scans over incident angle $\theta_{1a}$ of excitation light α relative to normal line N to a surface of metal film 220 in a side view of chip 200. Control section 140 also controls a second angle adjustment section so that light detection section 134 detects reflected light γ from above metal film 220. Reflected light γ reflected on metal film 220 reaches light detection section 134. Thus, control section 140 obtains data containing a relationship between incident angle $\theta_{1a}$ of excitation light α in a side view of chip 200 and light quantity of reflected light γ. After that, control section 140 analyzes the data and determines incident angle $\theta_{1a}$ at which light quantity of reflected light γ (of excitation light α) becomes minimum. When incident angle $\theta_{1a}$ of excitation light α is measured, incident angle $\theta_{1b}$ of excitation light α is set to 0°. Control section 140 determines incident angle $\theta_1$ ($\theta_{1a}$, $\theta_{1b}$) of excitation light α composed of $\theta_{1b}$ and incident angle $\theta_{1a}$ at which light quantity of reflected light γ (of excitation light α) becomes minimum.

Then, the fluorescence intensity of a first light is measured (step S230). Specifically, control section 140 irradiates a predetermined position of metal film 220 with excitation light α after providing a fluorescent labeling solution containing a secondary antibody labeled with a fluorescent substance, and simultaneously drives rotation section 320 to rotate (scan) first polarizer 114 around the optical axis of excitation light α as a central axis. In this step, incident angle $\theta_1$ ($\theta_{1a}$, $\theta_{1b}$) is the angle obtained in step S220. Control section 140 also adjusts a rotation angle of second polarizer 132 so that only the first light contained in fluorescence β is transmitted through. Light detection section 134 outputs a measured result (output $O_1$) to control section (processing section) 140. Output $O_1$ is the fluorescence intensity of the first light (e.g., light with an angle of an oscillation direction of the electric field of 0° relative to the plane), of fluorescence β emitted from a suspended fluorescent substance above metal film 220 (noise component).

Then, the fluorescence intensity of a second light is measured (step S240). Specifically, in the same manner as in step S230, control section 140 irradiates a predetermined position of metal film 220 with excitation light α and simultaneously drives rotation section 320 to rotate (scan) first polarizer 114 around the optical axis of excitation light α as a central axis. In this step, incident angle $\theta_1$ ($\theta_{1a}$, $\theta_{1b}$) is the angle obtained in step S220. Control section 140 also adjusts a rotation angle of second polarizer 132 so that only the second light contained in fluorescence β is transmitted through. Light detection section 134 outputs a measured result (output $O_2$) to control section (processing section) 140. Output $O_2$ is the fluorescence intensity of the second light (e.g., light with an angle of the oscillation direction of the electric field of 90° relative to the plane), of fluorescence β emitted from a suspended fluorescent substance above metal film 220 (noise component).

Then, control section 140 determines the polarization direction of excitation light α (step S250). Specifically, control section 140 obtains, from the measured results (output $O_1$ and output $O_2$) obtained in step S230 and step S240, the polarization direction of excitation light α when a difference value between the fluorescence intensity of the first light and the fluorescence intensity of the second light becomes zero. Thus, control section 140 determines the polarization direction of excitation light α as the direction in which a difference value between the fluorescence intensity of the first light and the fluorescence intensity of the second light becomes zero.

Control section 140, then adjusts the polarization direction of linearly polarized excitation light α (step S260). Specifically, control section 140 rotates first polarizer 114 so that the polarization direction of first polarizer 114 becomes the direction obtained in step S250.

Then, control section 140 reacts an analyte in a sample with a primary antibody while reacting the analyte with a labeled secondary antibody (primary reaction, secondary reaction: step S70).

As an optional step, metal film 220 is washed (step S80).

Then, the fluorescence intensity of a third light is measured (step S290). Specifically, control section 140 operates light source 112 to emit excitation light α. At the same time, control section 140 operates light detection section 134 to detect the intensity of fluorescence β from metal film 220. In this step, control section 140 adjusts a rotation angle of second polarizer 132 so that only the third light contained in fluorescence β (in the figure, light with an angle of an oscillation direction of the electric field of 0° relative to the plane) is transmitted through. Also, in this step, incident angle $\theta_1$ ($\theta_{1a}$, $\theta_{1b}$) is the angle obtained in step S220, and the polarization direction of first polarizer is the direction obtained in step S260. Light detection section 134 outputs a measured result (output Op) to control section (processing section) 140. Output Op contains a signal component and at least part of the fluorescent intensity of the first light.

Then, the fluorescence intensity of a fourth light is measured (step S300). Specifically, control section 140 operates light source 112 to emit excitation light α. At the same time, control section 140 operates light detection section 134 to detect the intensity of fluorescence β from metal film 220. In this step, control section 140 adjusts a rotation angle of second polarizer 132 so that only the fourth light contained in fluorescence β (in the figure, light with an angle of the oscillation direction of the electric field of 90° relative to the plane) is transmitted through. Also, in this step, incident angle $\theta_1$ ($\theta_{1a}$, $\theta_{1b}$) is the angle obtained in step S220, and the polarization direction of first polarizer 114 is the direction obtained in step S260. Light detection section 134 outputs a measured result (output Os) to control section (processing section) 140. Output Os is primarily at least part of the fluorescence intensity of the second light.

Finally, control section (processing section) 140 analyzes the output signals (outputs Op and Os) from light detection section 134, and analyzes the presence of an analyte or an amount of an analyte (step S310). Specifically, control section (processing section) 140 calculates a difference value between output Op and output Os to obtain a signal value.

Similar to the surface plasmon-field enhanced fluorescence measurement method according to Embodiment 1, the surface plasmon-field enhanced fluorescence measurement method according to Embodiment 2 can also accurately detect the fluorescence intensity of fluorescence β emitted from a fluorescent substance that labels an analyte even when the fluorescence intensity of the first light (of fluorescence β from a suspended fluorescent substance) and the fluorescence intensity of the second light (of fluorescence β from a suspended fluorescent substance) are different values.

As described above, SPFS apparatus 300 of the embodiment exerts the same advantageous effects as those exerted by SPFS apparatus 100 of Embodiment 1.

Figure 10:
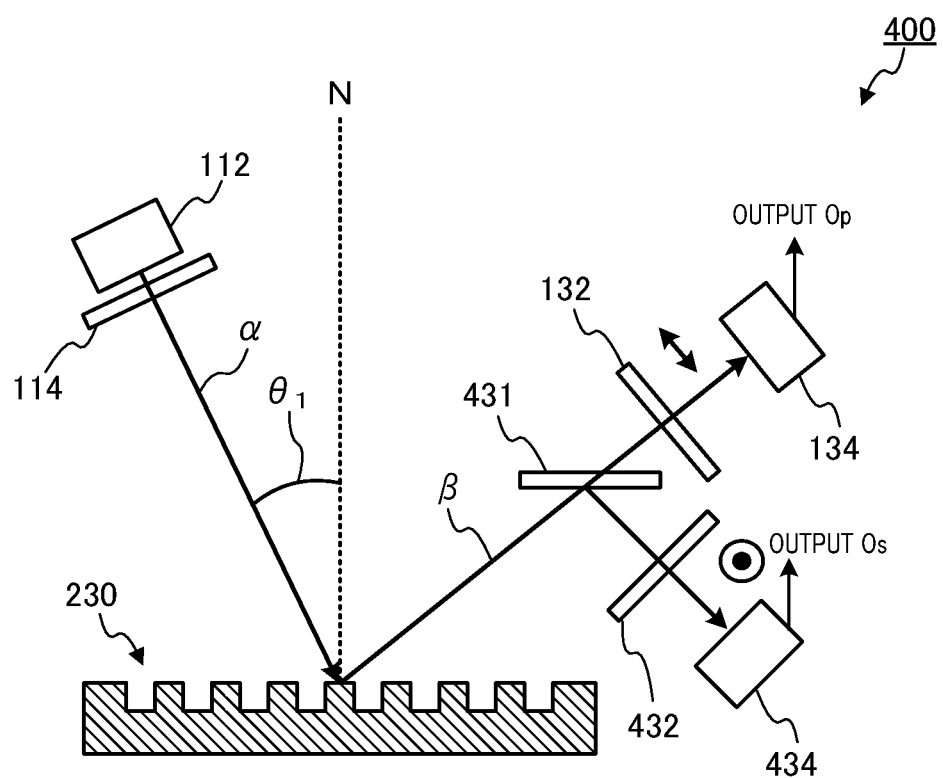
FIG. 10 is a schematic view illustrating another example of a configuration of a SPFS apparatus according to Embodiments 1 and 2.

In place of SPFS apparatus 100 illustrated in FIGS. 1 and 8, SPFS apparatus 400 illustrated in FIG. 10 may be used. As illustrated in FIG. 10, SPFS apparatus 400 is configured in the same manner as SPFS apparatuses 100 and 300 except that half-mirror 431, third polarizer 432, and light detection section 434 are further included.

Half-mirror 431 is disposed on the optical path of fluorescence β between diffraction grating 230 and second polarizer 132. Light detection section 434 is disposed on the optical path of fluorescence β reflected on half-mirror 431 (reflected light path), and third polarizer 432 is disposed on reflected light γ path between half-mirror 431 and light detection section 434. An rotation angle of second polarizer 132 is adjusted so that a first light and a third light (e.g., light with an angle of an oscillation of the electric field of 0° relative to the plane) are transmitted through, and an rotation angle of the third polarizer 432 is adjusted (or fixed) so that a second light and a fourth light (e.g., light with an angle of an oscillation of the electric field of 90° relative to the plane) are transmitted through. A polarizing beam splitter may be used in place of half-mirror 431, second polarizer 132, and third polarizer 432.

As described above, in addition to the same advantageous effects as those of SPFS apparatuses 100 and 300, SPFS apparatus 400 can simultaneously measure the first light and the second light, as well as the third light and the fourth light since half-mirror 431, third polarizer 432, and light detection section 434 are further included.

[Reference Experiment]

In this experiment, shown are investigated results of the polarization characteristics of fluorescence emitted from a fluorescent substance excited above a metal film (signal component indicating the presence or an amount of an analyte) and fluorescence emitted from a suspended fluorescent substance in a liquid (noise component) in a measurement apparatus and a measurement method utilizing GC-SPFS.

In the experiment, the directivity distribution of fluorescence emitted from a suspended fluorescent substance was investigated in the case in which incident angle $\theta_{1b}$ is 10° in a plan view of chip 200. In the experiment, a liquid containing only a fluorescent substance was provided to on metal film 220 without providing a sample containing an analyte. In the experiment, incident angle $\theta_{1a}$ of excitation light α in a side view of chip 200 was set to an angle at which light quantity of reflected light γ (of excitation light α) becomes minimum, and the polarization direction (angle) of excitation light α relative to a plane (containing normal line N to a surface of metal film 220 and the optical axis of excitation light α) was set to 0°. Under such conditions, diffraction grating 230 was irradiated with excitation light α having a predetermined wavelength. At the same time, the number of photons was measured for light, of fluorescence emitted from a suspended fluorescent substance, having an angle of an oscillation direction of the electric field of 0° relative to the plane, and for light, of the fluorescence emitted from a suspended fluorescent substance, having an angle of an oscillation direction of the electric field of 90° relative to the plane while a light receiving angle at light detection section 134 was changed. As a comparison, also measured was the number of photons for light with incident angle $\theta_{1b}$ of 0° in a plan view of chip 200 and an angle of an oscillation direction of the electric field of 0° relative to the plane.

Figure 11A:
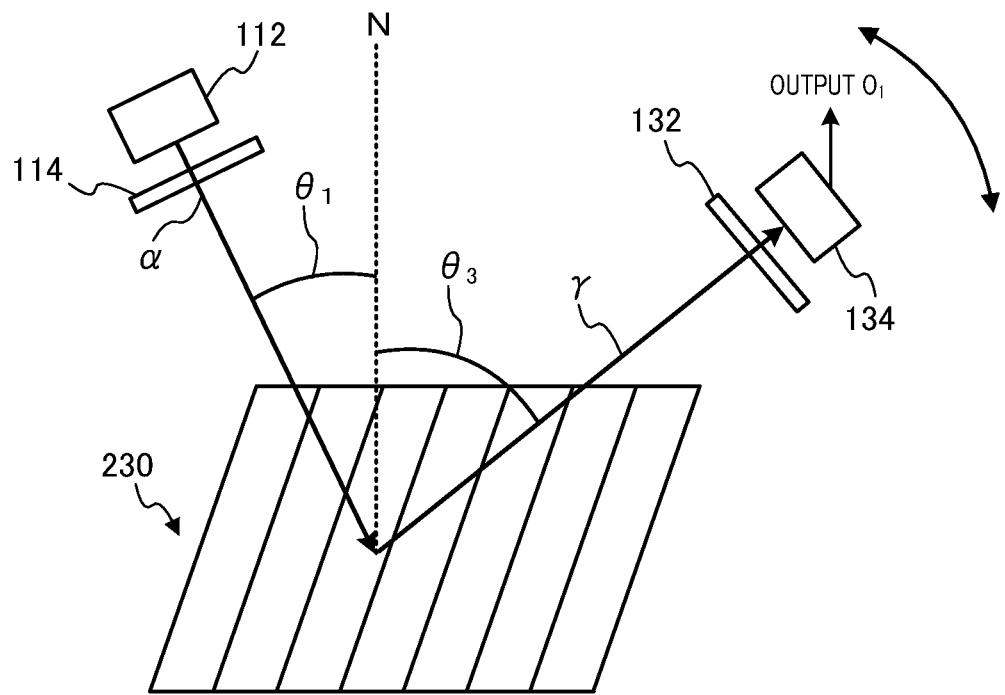
FIGS. 11A and 11B are schematic views illustrating a procedure of a reference experiment.
Figure 12A:
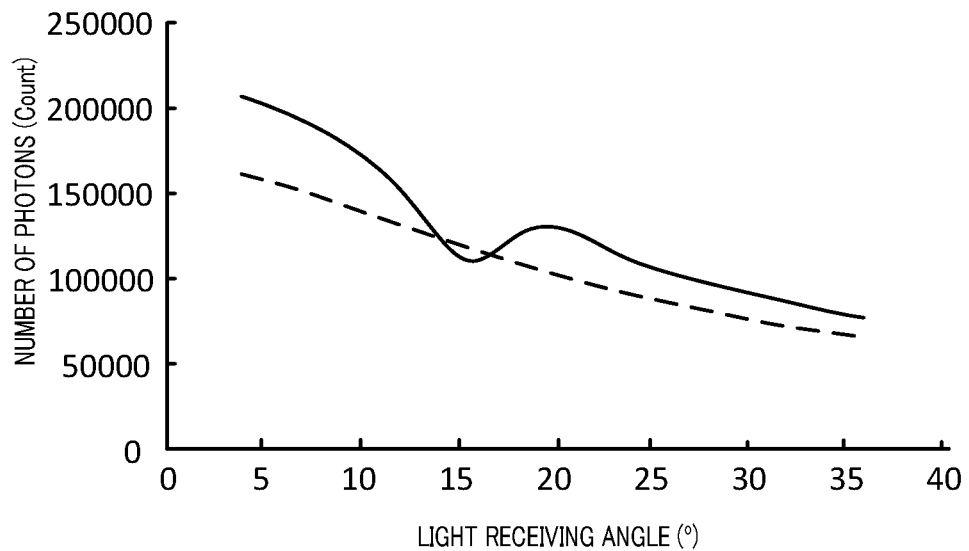
FIGS. 12A and 12B are graphs showing measured results of the reference experiment.

FIG. 11A is a schematic view illustrating a procedure of the reference experiment. FIG. 12A is a graph showing a relationship between a light receiving angle at light detection section 134 and the number of photons for fluorescence β emitted from a suspended fluorescent substance. In FIG. 12A, the horizontal axis is a light receiving angle $\theta_3$ (°) at light detection section 134, and the vertical axis is the number of photons (count) for fluorescence. In FIG. 12A, the solid line represents light with an angle of an oscillation direction of the electric field of 0° relative to the plane (at incident angle $\theta_{1b}$ of) 10°, and the broken line represents light with an angle of an oscillation direction of the electric field of 90° relative to the plane.

As shown in FIG. 11A and the solid line of FIG. 12A, the number of photons for light with an angle of an oscillation direction of the electric field of 0° relative to the plane temporarily lowered near the light receiving angle of 15°. In the case in which incident angle $\theta_{1b}$ is 10° in a plan view of chip 200, it was found that there exist light receiving angles at which a difference value becomes zero between the number of photons for light, originated from a suspended fluorescent substance, having an angle of an oscillation direction of the electric field of 0° relative to the plane, and the number of photons for light, originated from a suspended fluorescent substance, having an angle of an oscillation direction of the electric field of 90° relative to the plane. The light receiving angles at which the number of photons for light with an angle of an oscillation direction of the electric field of 0° relative to the plane temporarily lowered are the optimal light receiving angles for the detection of fluorescence β. The temporal lowering in the number of photons for light with an angle of an oscillation direction of the electric field of 0° relative to the plane is presumably due to temporal lowering in the intensity of enhanced electric fields at the light receiving angles.

Then, the directivity distribution of fluorescence emitted from a suspended fluorescent substance was investigated in the case where incident angle $\theta_{1b}$ is 90° in a plan view of chip 200. The other conditions are the same as those of the aforementioned experiment.

Figure 11B:
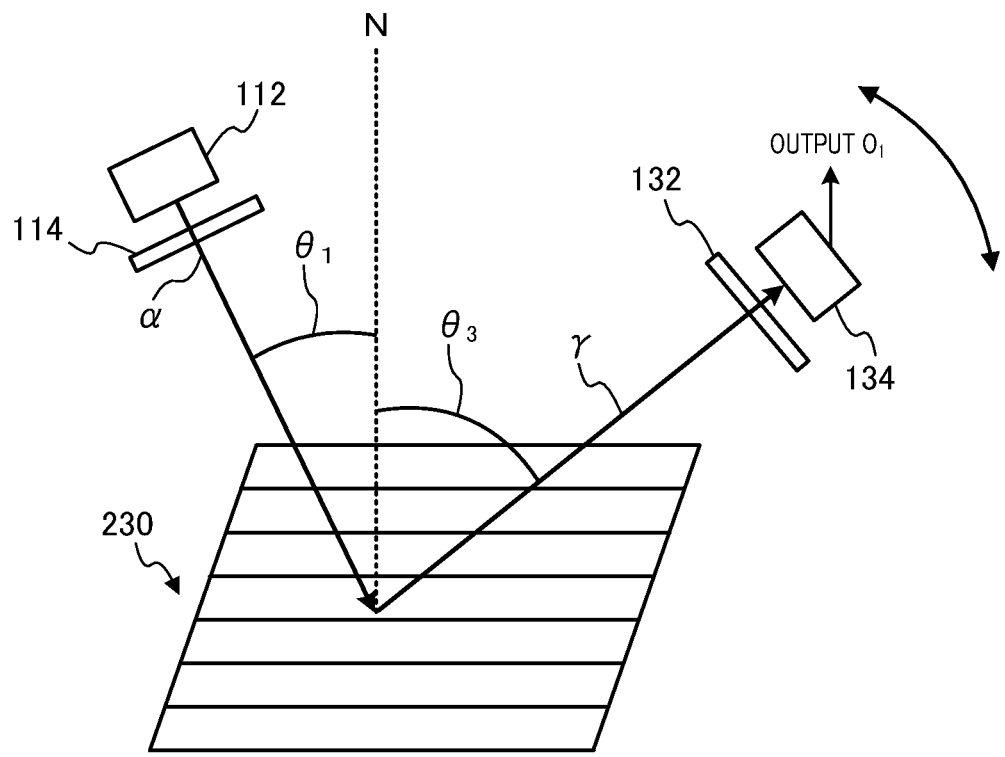
Figure 12B:
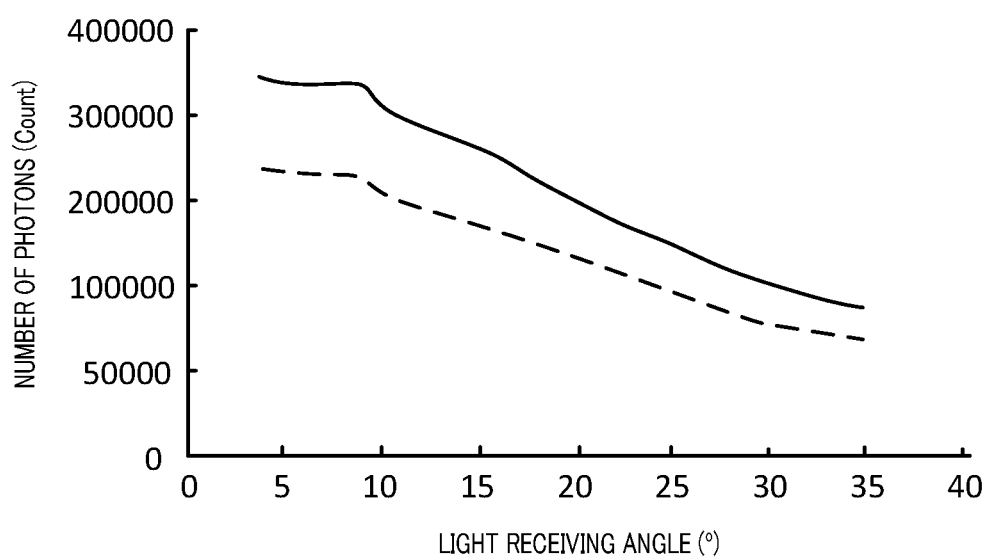

FIG. 11B is a schematic view illustrating a procedure of the reference experiment. FIG. 12B is a graph showing a relationship between a light receiving angle at light detection section 134 and the number of photons for fluorescence β. In FIG. 12B, the horizontal axis is a light receiving angle $\theta_3$ (°) at light detection section 134, and the vertical axis is the number of photons (count) for fluorescence. In FIG. 12B, the solid line represents light with an angle of an oscillation direction of the electric field of 0° relative to the plane, and the broken line represents light with an angle of an oscillation direction of the electric field of 90° relative to the plane.

As illustrated in FIG. 11B and the solid line and the broken line of FIG. 12B, in the case in which incident angle $\theta_{1b}$ is 90° in a plan view of chip 200, there was no temporal lowering in the number of photons for light with an angle of an oscillation direction of the electric field of 0° relative to the plane and for light with an angle of an oscillation direction of the electric field of 90° relative to the plane. Also, the number of photons for light with an angle of an oscillation direction of the electric field of 0° relative to the plane and the number of photons for light with an angle of an oscillation direction of the electric field of 90° relative to the plane were found to be different.

After that, investigated was a relationship between the polarization direction of excitation light α, and the fluorescence intensity of light with an angle of an oscillation direction of the electric field of 0° relative to the plane or the fluorescence intensity of light with an angle of an oscillation direction of the electric field of 90° relative to the plane.

In the experiment, incident angle $\theta_{1a}$ was set to 10°, and incident angle $\theta_{1b}$ was set to 0°. Under such conditions, diffraction grating 230 was irradiated with excitation light α having a predetermined wavelength. At the same time, the number of photons was measured for light, emitted from a suspended or an immobilized fluorescent substance, having an angle of an oscillation direction of the electric field of 0° relative to the plane, and for light having an angle of an oscillation direction of the electric field of 90° relative to the plane while the polarization direction of excitation light α was changed.

Figure 13A:
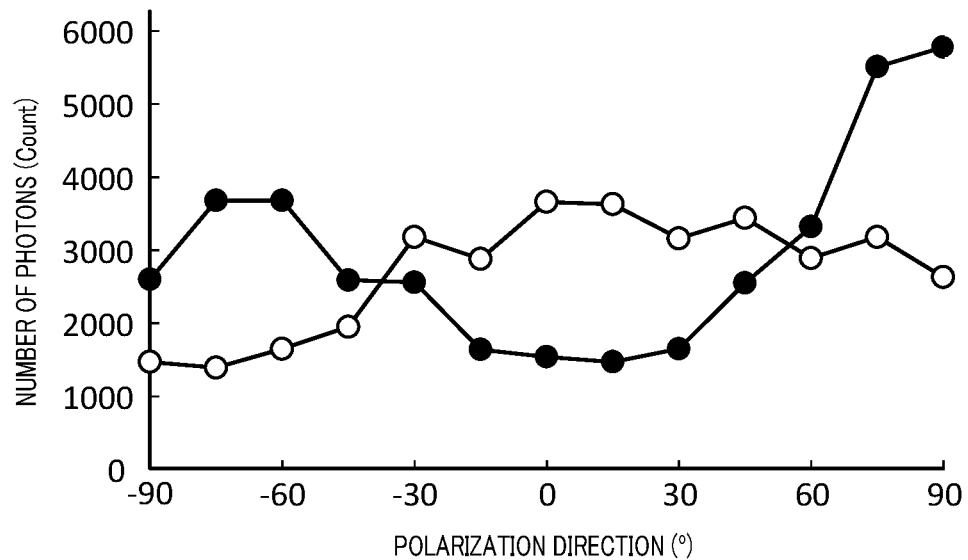
FIGS. 13A and 13B are graphs showing measured results of the reference experiment.

FIG. 13A is a graph showing a relationship between the polarization direction and the number of photons for fluorescence emitted from a fluorescent substance. In FIG. 13A, the horizontal axis represents the polarization direction (°) of excitation light α, and the vertical axis represents the number of photons (count) for fluorescence β. In FIG. 13A, black circle symbols represent a fluorescence component light, of fluorescence β, having an angle of an oscillation direction of the electric field of 0° relative to the plane, and white circle symbols represent a fluorescence component light, of fluorescence β, having an angle of an oscillation direction of the electric field of 90° relative to the plane.

As shown in FIG. 13A, the number of photons for light, of fluorescence β, having an angle of an oscillation direction of the electric field of 0° relative to the plane was maximum when excitation light α (light with an angle of an oscillation direction of the electric field of 0° relative to the plane) at incident angle $\theta_{1b}$ of 0° at which light quantity of reflected light γ (of excitation light α) becomes minimum was irradiated. Difference values between the number of photons for light with an angle of an oscillation direction of the electric field of 0° relative to the plane and the number of photons for light with an angle of an oscillation direction of the electric field of 0° relative to the plane were zero near the polarization direction of ±50°.

Then, investigated was the number of photons for fluorescence emitted from a fluorescent substance that labels an analyte when the polarization direction of excitation light α was changed. An analyte in a sample was labeled with Alexa Fluor fluorescent dye (Life Technologies Japan Ltd.) In this state, diffraction grating 230 was irradiated with excitation light α having a predetermined wavelength while the polarization direction of excitation light α was changed. At the same time, the number of photons for light, emitted from the fluorescent dye that labeled the analyte, having an angle of an oscillation direction of the electric field of 0° relative to the plane and the number of photons for light, emitted from the fluorescent dye that labeled the analyte, having an angle of an oscillation direction of the electric field of 90° relative to the plane were measured.

Figure 13B:
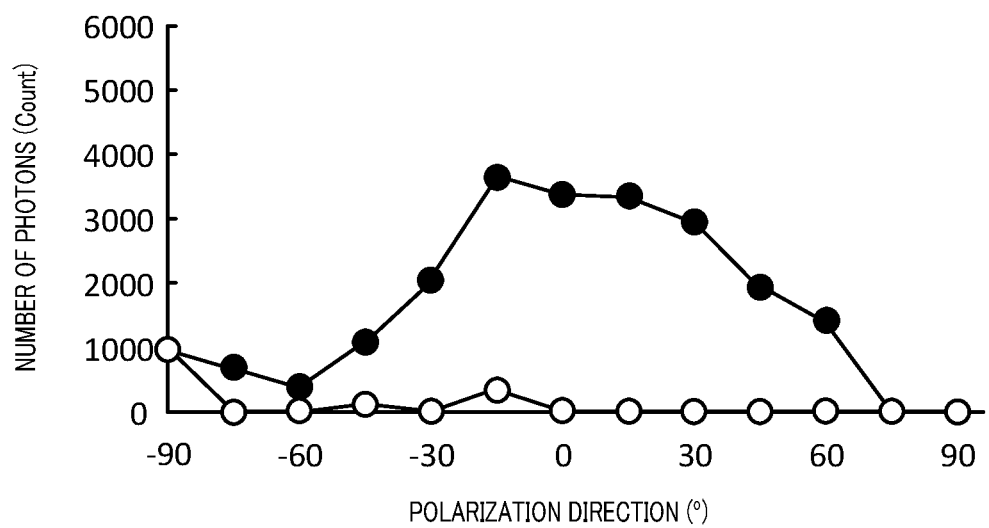

FIG. 13B is a graph showing a relationship between the polarization direction and the number of photons for fluorescence β. In FIG. 13B, the horizontal axis represents the polarization direction (°) of excitation light α, and the vertical axis represents the number of photons (count) for fluorescence β. In FIG. 13B, the black circle symbols represent light with an angle of an oscillation direction of the electric field of 0° relative to the plane, and the white circle symbols represent light with an angle of an oscillation direction of the electric field of 90° relative to the plane.

As shown in FIG. 13B, fluorescence β emitted from a fluorescent substance could be measured even when the polarization direction of excitation light α was around ±50°.

Accordingly, as shown in FIGS. 13A and 13B, a signal component value with little noise component can be calculated by subtracting a detected result of a light component with an angle of an oscillation direction of the electric field of 90° relative to the plane from a detected result of a light component with an angle of an oscillation direction of the electric field of 0° relative to the plane, even when a noise component other than a signal component is contained in fluorescence β.

This application is entitled to and claims the benefit of Japanese Patent Application No. 2014-253193, filed on Dec. 15, 2014, the disclosure of which including the specification, drawings and abstract is incorporated herein by reference in its entirety.

INDUSTRIAL APPLICABILITY

The surface plasmon-field enhanced fluorescence measurement apparatus and the surface plasmon-field enhanced fluorescence measurement method according to the embodiment can measure an analyte highly reliably, and thus are useful for clinical tests, for example.

The surface plasmon-field enhanced fluorescence measurement apparatus and the surface plasmon-field enhanced fluorescence measurement method according to the embodiment can also measure an analyte highly reliably without washing a metal film surface after a fluorescent labeling solution or the like is provided. Thus, the measurement apparatus and the measurement method according to the embodiment are expected to contribute to development, widespread use, and advancement of an extremely simple quantitative immunoassay system, as well as to the shortened measurement time.

REFERENCE SIGNS LIST 100, 300, 400 Surface plasmon-field enhanced fluorescence measurement apparatus (SPFS apparatus)
110 Excitation light irradiation unit
112 Light source
114 First polarizer
120, 320 Rotation section
122 Chip holder
124 Motor
130 Fluorescence detection unit
132 Second polarizer
134, 434 Light detection section
140 Control section (Processing section)
200 Chip
210 Substrate
220 Metal film
230 Diffraction grating
431 Half-mirror
432 Third polarizer
α Excitation light
β Fluorescence
γ Reflected light

The invention claimed is:

1. A surface plasmon-field enhanced fluorescence measurement apparatus equipped with a chip which includes a metal film and a diffraction grating formed in the metal film, the chip further including a ligand immobilized above the diffraction grating, the ligand being for capturing an analyte to be labeled with a fluorescent substance, the measurement apparatus detecting the presence or an amount of the analyte by irradiating the diffraction grating with excitation light, the measurement apparatus comprising:
a light source irradiating the diffraction grating with linearly polarized excitation light so that the fluorescent substance is excited by an enhanced electric field to emit fluorescence;
a rotation section controlling the direction of an optical axis of the excitation light relative to the diffraction grating in a plain view, and a polarization direction of the excitation light relative to the diffraction grating;
a polarizer isolating linearly polarized light from fluorescence emitted from the fluorescent substance; and
a light detection section detecting the linearly polarized light isolated by the polarizer.

2. The surface plasmon-field enhanced fluorescence measurement apparatus according to claim 1, further comprising a processing section processing a detected value obtained in the light detection section, wherein
the polarizer isolates, from fluorescence emitted from the fluorescent substance when a liquid containing the fluorescent substance is present on the metal film, first light with an angle of an oscillation direction of an electric field in the range of 0±30° relative to a plane and second light with an angle of an oscillation direction of an electric field in the range of 90±30° relative to the plane, the plane containing a normal line to a surface of the metal film and the optical axis of the excitation light, and
the polarizer isolates, from fluorescence emitted from the fluorescent substance when the analyte labeled with the fluorescent substance is captured by the ligand, third light with an angle of an oscillation direction of an electric field in the range of 0±30° relative to the plane and fourth light with an angle of an oscillation direction of an electric field in the range of 90±30° relative to the plane;
wherein the light detection section detects the first light and the second light when the liquid containing the fluorescent substance is present on the metal film, and detects the third light and the fourth light when the analyte labeled with the fluorescent substance is captured by the ligand;
wherein the processing section calculates a difference value between a detected value of the first light and a detected value of the second light when the liquid containing the fluorescent substance is present on the metal film, and calculates a difference value between a detected value of the third light and a detected value of the fourth light when the analyte labeled with the fluorescent substance is captured by the ligand; and
wherein the rotation section, before the light detection section detects the third light and the fourth light, relatively rotates one of the optical axis of the excitation light and the diffraction grating and the polarization direction of the excitation light and the diffraction grating so that the difference value, which is calculated in the processing section, between the detected value of the first light and the detected value of the second light becomes zero.

3. The surface plasmon-field enhanced fluorescence measurement apparatus according to claim 2, wherein the first light and the third light each have an angle of an oscillation direction of an electric field of 0° relative to the plane, and the second light and the fourth light each have an angle of an oscillation direction of an electric field of 90° relative to the plane.

4. The surface plasmon-field enhanced fluorescence measurement apparatus according to claim 1, wherein the rotation section changes the direction of the optical axis of the excitation light relative to the diffraction grating in a plan view.

5. The surface plasmon-field enhanced fluorescence measurement apparatus according to claim 1, wherein the rotation section changes the polarization direction of the excitation light relative to the diffraction grating in a plan view.

6. A surface plasmon-field enhanced fluorescence measurement method comprising:
a first step of preparing a chip which includes a metal film where a diffraction grating is formed in the metal film and which includes a ligand immobilized above the diffraction grating, the ligand being for capturing an analyte to be labeled with a fluorescent substance;
a second step of irradiating the diffraction grating with linearly polarized excitation light, when a liquid containing the fluorescent substance is present on the metal film, so as to generate surface plasmon resonance in the diffraction grating; detecting linearly polarized first light with an angle of an oscillation direction of an electric field in the range of 0±30° relative to a plane and linearly polarized second light with an angle of an oscillation direction of an electric field in the range of 90±30° relative to the plane, the plane containing a normal line to a surface of the metal film and an optical axis of the excitation light, the linearly polarized first light and the linearly polarized second light being contained in fluorescence emitted from the fluorescent substance; and changing a direction of the optical axis of the excitation light relative to the diffraction grating in a plan view or changing a polarization direction of the excitation light relative to the diffraction grating so that a difference value between a detected value of the first light and a detected value of the second light becomes zero;

a third step of bringing the analyte labeled with the fluorescent substance into contact with the ligand immobilized above the metal film or labeling the analyte captured by the ligand immobilized above the metal film with the fluorescent substance;

a fourth step of irradiating, after the second step and the third step, the diffraction grating with linearly polarized excitation light so as to generate surface plasmon resonance in the diffraction grating, and detecting linearly polarized third light with an angle of an oscillation direction of an electric field in the range of 0±30° relative to the plane and linearly polarized fourth light with an angle of an oscillation direction of an electric field in the range of 90±30° relative to the plane, the linearly polarized third light and the linearly polarized fourth light being contained in fluorescence emitted from the fluorescent substance; and a fifth step of calculating a difference value between a detected value of the third light and a detected value of the fourth light.

7. The surface plasmon-field enhanced fluorescence measurement method according to claim 6, wherein
the first light and the third light each have an angle of an oscillation direction of an electric field of 0° relative to the plane, and
the second light and the fourth light each have an angle of an oscillation direction of an electric field is 90° relative to the plane.

8. The surface plasmon-field enhanced fluorescence measurement method according to claim 6, wherein the second step changes the direction of the optical axis of the excitation light relative to the diffraction grating in a plan view.

9. The surface plasmon-field enhanced fluorescence measurement method according to claim 6, wherein the second step changes the polarization direction of the excitation light relative to the diffraction grating in a plan view.

* * * * *